United States Patent [19]

Willey et al.

[11] Patent Number: 5,686,015

[45] Date of Patent: *Nov. 11, 1997

[54] QUATERNARY SUBSTITUTED BLEACH ACTIVATORS

[75] Inventors: Alan David Willey, Cincinnati; Gregory Scot Miracle, Forest Park; Kevin Lee Kott, Cincinnati; Michael Eugene Burns, West Chester, all of Ohio; Gerard Marcel Abel Baillely, Newcastle Upon Tyne, United Kingdom; Nour-Eddine Guedira, Newcastle Upon Tyne, United Kingdom; Frederick Edward Hardy, Newcastle Upon Tyne, United Kingdom; Lucille Florence Taylor, Middletown; Mark Robert Sivik, Fairfield, both of Ohio

[73] Assignee: The Procter & Gamble Company, Cincinnati, Ohio

[*] Notice: The term of this patent shall not extend beyond the expiration date of Pat. No. 5,460,747.

[21] Appl. No.: 298,903

[22] Filed: Aug. 31, 1994

[51] Int. Cl.$^6$ .............. C09K 3/00; C01B 15/055; C11D 3/39; C11D 3/395

[52] U.S. Cl. .............. 252/186.39; 252/186.38; 252/186.33; 252/186.27; 510/312; 510/313; 510/311

[58] Field of Search .............. 252/186.38, 186.39, 252/186.33, 186.43, 186.3, 186.27, 94, 99, 102; 510/311, 312, 313

[56] References Cited

U.S. PATENT DOCUMENTS

| | | | |
|---|---|---|---|
| 3,816,324 | 6/1974 | Fine et al. | 252/186.38 |
| 3,988,433 | 10/1976 | Benedict | 424/53 |
| 4,115,060 | 9/1978 | Finley et al. | 8/111 |
| 4,210,551 | 7/1980 | Brubaker | 252/186.38 |
| 4,260,529 | 4/1981 | Letton | 510/350 |
| 4,367,156 | 1/1983 | Diehl | 510/313 |
| 4,397,757 | 8/1983 | Bright et al. | 252/186.41 |
| 4,451,384 | 5/1984 | Malafosse | 510/314 |
| 4,539,130 | 9/1985 | Thompson et al. | 510/376 |
| 4,551,263 | 11/1985 | Schellhammer et al. | 252/186.39 |
| 4,728,455 | 3/1988 | Rerek | 510/303 |
| 4,751,015 | 6/1988 | Humphreys et al. | 510/376 |
| 4,818,426 | 4/1989 | Humphreys et al. | 510/375 |
| 4,904,406 | 2/1990 | Darwent et al. | 510/376 |
| 4,933,103 | 6/1990 | Aoyagi et al. | 252/186.38 |
| 4,988,451 | 1/1991 | Nunn et al. | 510/312 |
| 5,059,344 | 10/1991 | Aoyagi et al. | 252/186.38 |
| 5,093,022 | 3/1992 | Sotoya et al. | 510/376 |
| 5,106,528 | 4/1992 | Francis et al. | 252/186.23 |
| 5,143,641 | 9/1992 | Nunn | 252/186.38 |
| 5,245,075 | 9/1993 | Venturello et al. | 510/375 |
| 5,269,962 | 12/1993 | Brodbeck et al. | 252/186.25 |
| 5,294,362 | 3/1994 | Venturello et al. | 510/310 |
| 5,405,413 | 4/1995 | Willey et al. | 8/111 |
| 5,460,747 | 10/1995 | Gosselink et al. | 252/186.38 |
| 5,534,196 | 7/1996 | Chapman et al. | 252/186.27 |
| 5,578,136 | 11/1996 | Taylor et al. | 134/25.2 |
| 5,584,888 | 12/1996 | Miracle et al. | 8/111 |

FOREIGN PATENT DOCUMENTS

| | | | |
|---|---|---|---|
| 170386 | 2/1986 | European Pat. Off. | C11D 3/39 |
| 284 292 | 3/1988 | European Pat. Off. | 3/39 |
| 403152 | 12/1990 | European Pat. Off. | C11D 3/39 |
| 427224 | 5/1991 | European Pat. Off. | C07C 229/16 |
| 458396 A1 | 5/1991 | European Pat. Off. | 3/39 |
| 475 512 A1 | 9/1991 | European Pat. Off. | 219/4 |
| 2-115154 | 10/1988 | Japan | C07C 237/52 |
| 2132195 | 5/1990 | Japan | C11D 3/39 |
| 2182795 | 7/1990 | Japan | C11D 3/39 |
| 4164056 | 6/1992 | Japan | C07C 237/52 |
| 1382594 | 2/1975 | United Kingdom . | |
| 2270690 | 3/1994 | United Kingdom | C07D 209/48 |
| WO 94/01399 | 1/1994 | WIPO | 409/40 |
| WO 94/02597 | 2/1994 | WIPO . | |
| WO 94/07944 | 4/1994 | WIPO . | |
| WO 94/28106 | 12/1994 | WIPO | C11D 3/39 |
| WO 95/14760 | 6/1995 | WIPO | C11D 3/39 |

*Primary Examiner*—Joseph D. Anthony
*Attorney, Agent, or Firm*—Brian M. Bolam; Michael D. Jones; Kim William Zerby

[57] ABSTRACT

Bleaching compositions, laundry and automatic dishwashing detergent compositions comprising particular quaternary-substituted bleach activators, are provided. More specifically, the invention relates to compositions which provide enhanced cleaning/bleaching benefits though the selection of quaternary-substituted bleach activators having specific leaving groups with a conjugate acid pKa above 13 and with specific ratios of the rate of perhydrolysis to the rate of hydrolysis and the rate of perhydrolysis to the rate of diacylperoxide production. Included are preferred activator compounds and methods for washing fabrics, hard surfaces, and tableware using the activators.

30 Claims, No Drawings

QUATERNARY SUBSTITUTED BLEACH ACTIVATORS

FIELD OF THE INVENTION

The present invention relates to bleaching compositions comprising quaternary substituted bleach activator compounds comprising at least one tetravalent nitrogen. The compositions boost the performance of bleaching agents such as perborate. The multiple-substituted bleach activators are useful in fabric laundry and bleaching compositions, automatic dishwashing compositions, hard surface cleaners, bleach additives and the like.

BACKGROUND OF THE INVENTION

The formulation of detergent compositions which effectively remove a wide variety of soils and stains from fabrics under wide-ranging usage conditions remains a considerable challenge to the laundry detergent industry. Challenges are also faced by the formulator of automatic dishwashing detergent compositions (ADD's), which are expected to efficiently cleanse and sanitize dishware, often under heavy soil loads. The problems associated with the formulation of truly effective cleaning and bleaching compositions have been exacerbated by legislation which limits the use of effective ingredients such as phosphate builders in many regions of the world.

Most conventional cleaning compositions contain mixtures of various detersive surfactants to remove a wide variety of soils and stains from surfaces. In addition, various detersive enzymes, soil suspending agents, non-phosphorus builders, optical brighteners, and the like may be added to boost overall cleaning performance. Many fully-formulated cleaning compositions contain oxygen bleach, which can be a perborate or percarbonate compound. While quite effective at high temperatures, perborates and percarbonates lose much of their bleaching function at the low to moderate temperatures increasingly favored in consumer product use. Accordingly, various bleach activators such as tetraacetylethylenediamine (TAED) and nonanoyloxybenzenesulfonate (NOBS) have been developed to potentiate the bleaching action of perborate and percarbonate across a wide temperature range. NOBS is particularly effective on "dingy" fabrics.

Despite the use of TAED and NOBS in various cleaning and bleaching compositions, the search continues for more effective activator materials, especially for cleaning additional types of soils and surfaces. Improved activator materials should be safe, effective, and will preferably be designed to interact with troublesome soils and stains. Various cationically charged activators have been described in the literature. Many are esoteric and expensive. Some do not appear to be sufficiently compatible with anionic surfactants to allow their easy formulation into detergent compositions and yield a truly effective surfactant-plus-activated bleach system. The majority of cationic activators in the literature have a conjugate acid aqueous $pK_a$ value of the leaving-group which is below 13. It is generally accepted that bleach activators having leaving-groups with $pK_a$ values below 13 perhydrolyze at a desirable rate.

It has now been determined that certain selected quaternary substituted bleach activators (QSBA's hereinafter) are unexpectedly effective in removing soils and stains from fabrics and hard surfaces such as dishes despite having a leaving- group conjugate acid aqueous $pK_a$ of greater than 13. These activators have advantageously high ratios of rates of perhydrolysis to hydrolysis and of perhydrolysis to diacylperoxide formation. Without being limited by theory, these unusual rate ratios lead to a number of significant benefits for the instant QSBA's, including increased efficiency, avoidance of wasteful byproduct formation in the wash, increased color compatibility, increased enzyme compatibility, and better stability on storage. Commercially attractive QSBA's are provided, for example through the use of caprolactam-based chemistry.

The QSBA's herein are effective for removing soils and stains not only from fabrics, but also from dishware in automatic dishwashing compositions. The activators are designed to function well over a wide range of washing or soaking temperatures and are safe on rubber surfaces, such as those of sump hoses often used in European front-loading washing machines. In short, the QSBA's herein provide a substantial advance over activators known in the art, as will be seen from the disclosures hereinafter.

BACKGROUND ART

Cationic bleaches and bleach activators of various types are described in U.S. Pat. Nos. 4,904,406; 4,751,015; 4,988,451; 4,397,757; 5,269,962; 5,127,852; 5,093,022; 5,106,528; U.K. 1,382,594; EP 475,512, 458,396 and 284,292; and in JP 87-318,332 and JP 88-115,154.

SUMMARY OF THE INVENTION

The present invention encompasses bleaching compositions comprising: (a) an effective amount of a source of hydrogen peroxide; and (b) an effective amount of a quaternary substituted bleach activator comprising: (I) quaternary moieties QC(X)L, wherein X is selected from the group consisting of =O, =N—and =S; and (II) a charge-balancing number of compatible counterions.

L, the leaving group of the quaternary substituted bleach activator, when considered as the conjugate acid, LH, is non-charged or anionically charged, preferably non-charged, comprising at least one tri-coordinate nitrogen atom covalently connecting L to the moiety —C(X)—, for example as in the structure fragment:

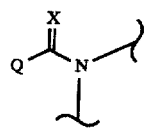

In general, the conjugate acid aqueous $pK_a$ of L with respect to the tri-coordinate nitrogen atom is about 13 or greater.

Q comprises a tetravalent nitrogen atom, $N^+$, wherein the tetravalent nitrogen atom is covalently connected to the moiety —C(X)L in QC(X)L by a single, double, or triple aliphatic, aromatic or aliphatic/aromatic linkage, as illustrated in all the following embodiments of quaternary substituted bleach activators within the scope of the invention:

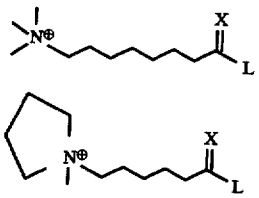

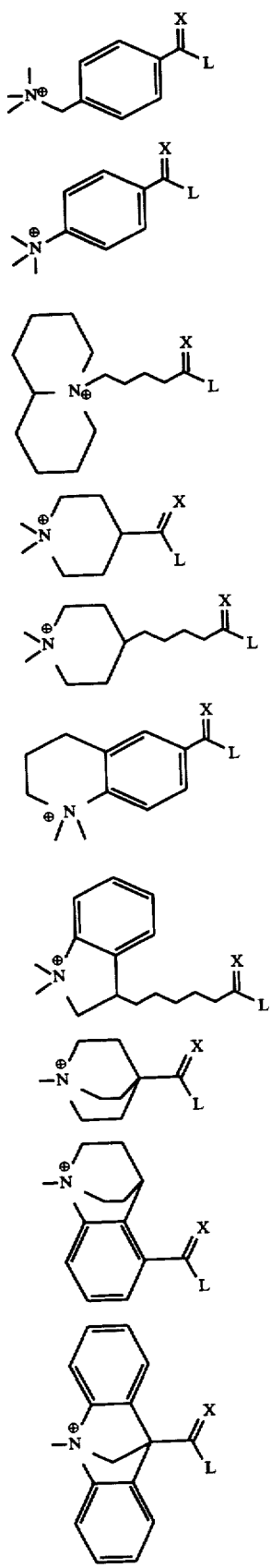

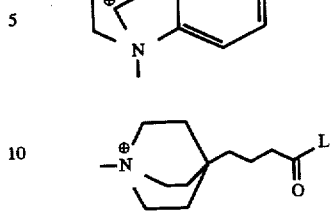

When the linkage is aliphatic, the linkage comprises at least two carbon atoms between the tetravalent nitrogen atom and the moiety —C(X)—, as in the following illustration depicting an acceptable structure on the left and an unacceptable one on the right:

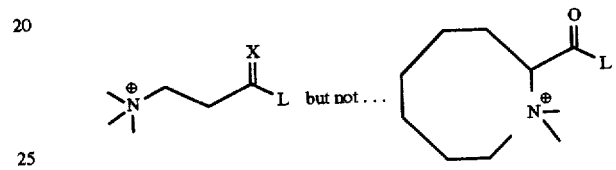

In general, the atom in Q to which moiety —C(X)— is bonded is a carbon atom:

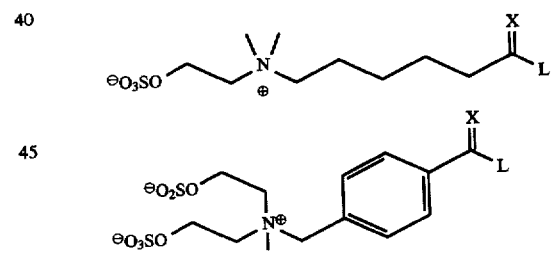

Although Q preferably contains no charged moieties other than said tetravalent nitrogen, structures wherein Q contains additional charges are within the general scope. Two such less preferred embodiments are illustrated below:

Importantly, the quaternary substituted bleach activators of this invention have a ratio of: (i) $k_P/k_H \geq 1$ wherein $k_P$ is the rate constant for perhydrolysis of the quaternary substituted bleach activator and $k_H$ is the rate constant for hydrolysis of the quaternary substituted bleach activator; and a ratio of:

(ii) $k_P/k_D \geq 5$ wherein $k_P$ is as defined in (i) and wherein $k_D$ is the rate constant for the formation of a diacylperoxide from the quaternary substituted bleach activator. In general, $k_H \leq 10 M^{-1} s^{-1}$, preferably $kH \leq 5M^{-1}s^{-1}$.

In a preferred embodiment, L is non-charged; Q contains no charged moieties other than said tetravalent nitrogen; said compatible counter-ions are anions or polyanions; X is O; the $pK_a$ of L as measured in DMSO is less than or equal to about 33, more preferably less than or equal to 28; $k_P/k_H \geq 2$.

more preferably $k_P/k_H \geq 10$, most preferably $k_P/k_H \geq 100$; and $k_P/k_D \geq 50$.

Quaternary substituted bleach activators of this invention preferably have a perhydrolysis efficiency, as defined hereinafter, of at least 10%, preferably at least 20%. In still other preferred embodiments, L together with —C(X)— forms an imide group.

The preferred compatible counter-ions are anions or polyanions, nonlimitingly illustrated by a member selected from the group consisting of polyacrylate, polymaleate, copolymers of maleate and acrylate, chloride, p-toluenesulfonate, methanesulfonate, napthalenesulfonate and cumenesulfonate. Highly preferred counterions are selected from the group consisting of chloride and p-toluenesulfonate. Mixtures of counter-ions are included. Highly preferred counter-ions are non-surface active, are resistant to precipitation in the presence of QSBA cations or water calcium or magnesium hardness, and, even more desirably, have an independent detergent utility such as soil dispersancy. The most highly preferred counter-ions are inert under the oxidation/reduction conditions of consumer detergent product use.

In still another preferred embodiment, the bleaching compositions of this invention comprise quaternary bleach activators wherein Q is selected from $R^1R^2R^3N^+T$ wherein $R^1$, $R^2$ and $R^3$ can vary independently and each R moiety is selected from the group consisting of: H; methyl; ethyl; $C_n$ linear or branched, substituted or unsubstituted alkyl wherein n is from 3 to about 16; aryl; substituted aryl; alkaryl; substituted alkaryl; and ethoxylated alkyl; and T is selected from the group consisting of: —(CH2)$_i$— wherein i is from about 3 to about 12; —(CH$_2$)$_i$(C$_6$H$_4$)(CH$_2$)$_j$— wherein i and j are independently from 0 to about 12 provided that at least one of i and j is nonzero and the polyalkylene substituents attached to $C_6H_4$ are o-, m- or p- to each other; -(Aryl)-; -(Alkyl)G(Aryl)-; -(Alkyl)G(Alkyl)-; -(Aryl)G(Alkyl)-; and -(Aryl)G(Aryl)- ; wherein G is selected from O, —C(O)N(R$^4$)—, —S(O)$_2$N(R$^4$)—, —N(R$^4$)C(O)—, —N(R$^4$)S(O)$_2$—, —S(O)$_2$— and —N(R$^4$)C(O)N(R$^5$)— wherein $R^4$ and $R^5$ are H or alkyl.

Note that the term "alkaryl" as used herein encompasses both alkyl-aryl and aryl-alkyl moieties, i.e., unless otherwise noted, alkyl and aryl can be "flipped".

The structures of simple, nonlimiting examples of preferred quaternary substituted bleach activators of these types is readily appreciated by considering the following preferred sub-group from which the quaternary substituted bleach activator may be selected: $R^1R^2R^3N^+TC(O)L$; $R^1R^2N^+(TC(O)L)_2$; $R^1N^+(TC(O)L)_3$; and mixtures thereof, preferably the first of these three, wherein $R^1$, $R^2$ and $R^3$ can vary independently and are selected from: H, methyl, ethyl, phenyl, benzyl, 1-naphthylmethylene and 2-naphthylmethylene; said moieties T are the same or different and are selected from m-C$_6$H$_4$, p-C$_6$H$_4$, —(CH$_2$)$_i$(m-C$_6$H$_4$)—, and —(CH$_2$)$_i$(p-C$_6$H$_4$)—; wherein i is from 1 to about 6.

In certain highly preferred embodiments, the atom directly connecting $R_1R_2R_3N^+T$ to —C(O)L is an aromatic carbon atom. When such a quaternary substituted bleach activator is perhydrolyzed, an aromatic peracid is formed which has excellent bleaching and stain-removing effectiveness.

In general, the tetravalent nitrogen atom of Q can be part of one or more rings. These rings may be unsaturated or saturated, and typically contain one or more of carbon, nitrogen, and oxygen with the tetravalent nitrogen either directly incorporated therein or present in a side-chain.

This invention also encompasses bleaching systems comprising at least about 0.1%, preferably from about 0.1% to about 50%, by weight, of a quaternary substituted bleach activator as defined herein, and at least about 0.1%, preferably from about 0.1% to about 50%, by weight, of a source of hydrogen peroxide. Optionally, but preferably the bleaching system further comprises at least 0.1%, preferably from about 0.1% to about 10% of a chelant.

In further embodiments, the invention encompasses laundry detergent compositions, for example those which comprise: a) from about 0.1% to about 10% of said quaternary substituted bleach activator; b) from about 0.5% to about 25% of said source of hydrogen peroxide, preferably in the form of a perborate or percarbonate salt; and c) from about 0.5% to about 25% of a detersive surfactant as disclosed hereinafter, preferably selected from the group consisting of sugar-derived surfactants (especially alkylpolyglycosides or glucosamides); amine oxides; sarcosinates (such as oleyl sarcosinate); and mixtures thereof. There may be optionally included (c) one or more detersive adjuncts. Preferred fully-formulated laundry detergents include phosphate-free, chlorine-bleach free granules.

The invention likewise encompasses automatic dishwashing compositions, including granules, comprising: (a) from about 0.1% to about 10% of said quaternary substituted bleach activator; (b) from about 0.5% to about 25% of said source of hydrogen peroxide in the form of a perborate or percarbonate salt; (c) from about 0.1% to about 7% of a low-foaming surfactant; (d) optionally, one or more detergency builders; and (e) optionally, one or more detersive adjuncts of types generally suited for automatic dishwashing.

In the various detergent compositions herein, it is often found useful to incorporate ethoxylated nonionic surfactants, either alone or in combination with other surfactants, owing to the known hard water resistance of the ethoxylate types.

The invention also encompasses hard-surface cleaning and liquid bleach or bleach additive compositions, such as one comprising (a) a quaternary substituted bleach activator, typically at levels of from about 2% to about 10%; and (b) one or more bleach stable thickeners. In the more acidic formulations, hydrogen peroxide may most readily be stably coformulated, especially with the additional stabilizing effect of an added chelating agent. Phase boundaries can of course also be used for additional kinetic stabilization by separating activator and hydrogen peroxide components. In acidic environments, it should be recognized that additional quaternization of trivalent nitrogen is possible, forming "acid salts". These remain within the spirit and scope of the invention, since on raising the pH (as in use), bleach activator structures such as those explicitly illustrated herein will rapidly be reformed. Most commonly, the bleaching compositions herein are alkaline solids, with a general pH range (1% solution) of from about 7 to about 12, more typically from about 8 to about 11.

Preferred bleaching compositions may further comprise at least one anionic surfactant. When they do so, it is preferable that the anionic surfactant as a whole should comprise no more than about 20%, more preferably no more than about 1%, of calcium-precipitable fatty acid. A convenient test for best anionic surfactant compatibility is to form an aqueous solution of the anionic surfactant with the quaternary substituted bleach activator. A preferred anionic surfactant forms no visible precipitate on mixing at ambient temperature.

Detersive builders are useful in the instant bleaching compositions. Preferred builders are selected from the group consisting of citrate, layered silicate, zeolite A, zeolite P and mixtures thereof.

The bleaching composition of this invention may further comprise conventional bleach activators. The term "conventional bleach activator" in general as used herein refers to any known bleach activator other than the herein-defined quaternary substituted bleach activators. Highly preferred conventional bleach activators are selected from the group consisting of alkanoyloxybenzenesulfonates, tetraacetylethylenediamine, and mixtures thereof. The bleaching composition of this invention may further comprise transition-metal containing bleach catalysts, as further illustrated in detail hereinafter.

The invention also encompasses a method for removing stains from fabrics or hard surfaces, especially dishware, comprising contacting said stains with a source of hydrogen peroxide and a quaternary bleach activator compound as defined herein in the presence of water, preferably with agitation. Typically the activator will be present at levels of at least about 20 ppm in the water. The source of hydrogen peroxide will preferably be present at levels of at least 50 ppm.

The invention is not limited to the bleaching or cleaning composition embodiments but further encompasses numerous novel chemical substances including, but not limited to, quaternary substituted bleach activators having formulas selected from:

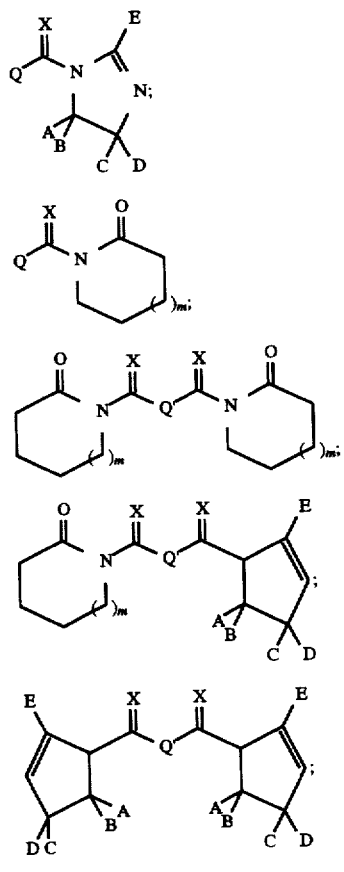

and mixtures thereof;

wherein A, B, C, D and E are independently selected from the group consisting H, substituted or unsubstituted alkyl, ethoxylated alkyl, linear alkyl, aryl, alkaryl, substituted alkaryl, substituted aryl, and mixtures thereof; and m is 1 or 2; and wherein Q is $R^1R^2R^3N^+T$ and Q' is $R^1R^2N^+(T)_2$ wherein $R^1$, $R^2$ $R^3$ can vary independently and each of said R moieties is selected from the group consisting of: H; methyl; ethyl; $C_n$ linear or branched, substituted or unsubstituted alkyl wherein n is from 3 to about 16; aryl; substituted aryl; alkaryl; substituted alkaryl; and ethoxylated alkyl; and T is selected from the group consisting of: —$(CH_2)i$— wherein i is from about 3 to about 12; —$(CH_2)_i$ $(C_6H_4)(CH_2)_j$— wherein i and j are independently from 0 to about 12 provided that at least one of i and j is nonzero and the polyalkylene substituents attached to $C_6H_4$ are o-, m- or p- to each other; -(Aryl)-; -(Alkyl)G(Aryl)-; -(Alkyl)G (Alkyl)-; -(Aryl)G(Alkyl)-; and -(Aryl)G(Aryl)-; wherein G is selected from O, —$C(O)N(R^4)$—, —$S(O)_2N(R^4)$—, —$N(R^4)C(O)$—, —$N(R^4)S(O)_2$—, —$S(O)_2$— and —$N(R^4)$ $C(O)N(R^5)$— wherein $R^4$ and $R^5$ are H or alkyl. Of the above, compounds (I), (II) and mixtures thereof are highly preferred.

With reference to the 4,5 saturated amidine structure, such as in (I) above, E is H, substituted or unsubstituted alkyl, ethoxylated alkyl, linear alkyl, aryl, alkaryl, substituted alkaryl, substituted aryl, and mixtures thereof. A, B, C, and D are independently selected from the group consisting of H, aryl, substituted aryl, alkaryl, ethoxylated alkyl, substituted alkaryl and linear or branched substituted or unsubstituted alkyl. More preferably still, E is selected from H and linear $C_1$–$C_4$ alkyl, most preferably methyl, and A, B, C and D are hydrogen.

By "effective amount" herein is meant an amount which is sufficient, under whatever comparative test conditions are employed, to enhance cleaning of a soiled surface. Likewise, the term "catalytically effective amount" refers to an amount which is sufficient under whatever comparative test conditions are employed, to enhance cleaning of a soiled surface.

All percentages, ratios and proportions herein are by weight, unless otherwise specified. All documents cited are, in relevant part, incorporated herein by reference.

DETAILED DESCRIPTION OF THE INVENTION

The present invention includes QSBA's and bleaching compositions comprising same nonlimitingly illustrated by laundry detergents, bleach additives and the like in various forms including liquids, gels, powders, granules and tablets.

Quaternary—Unless otherwise noted, the terms "quaternary" or "tetravalent" refer to nitrogen atoms which participate in either four single bonds, two single bonds and a double bond, one single bond and a triple bond, or two double bonds. In general, bonds to tetravalent nitrogen herein can include N—H bonds and other bonds, such as N—O bonds. In highly preferred QSBA's, all bonds in which each tetravalent or quaternary nitrogen atom participates are bonds to carbon atoms:

Preferred Quaternary Substituted Bleach Activators—A simple example of a preferred activator compound has the formula:

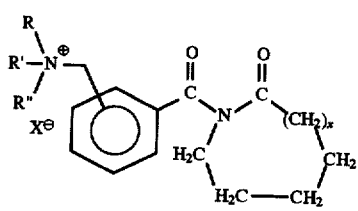

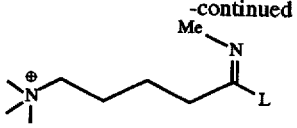

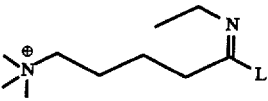

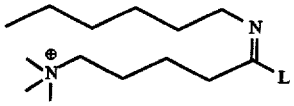

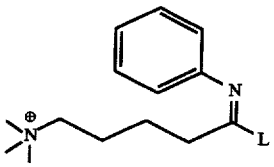

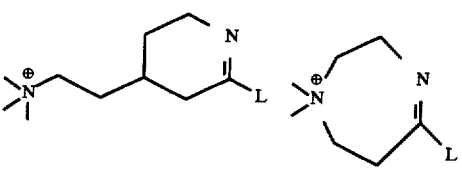

In the above formula, substituents R, R' and R" may each be $C_1$–$C_{10}$ alkyl groups. Some preferred compounds in accordance with this formula are those wherein R, R' and R" are each $C_1$–$C_3$, especially wherein all R groups are methyl or ethyl. When x is zero, these compounds are derived from valerolactam. When x is one, they are derived from caprolactam. The nature of anion X in the above compounds is of no special significance, in the sense that X may vary widely. Thus, X may be, for example, chloride, methylsulfate, bromide, or any other convenient anion, according to the desires of the formulator. As indicated by the structural formula, the quaternary ammonium group may be ortho, meta or para (preferred) to the carbonyl substituent. With respect to the moieties X, L, and Q in the quaternary bleach activator structures encompassed herein, further illustration may assist the practitioner.

Moieties X—When X is =O or =S, it is immediately apparent what structures are encompassed. When X is =N— however, the following structures further illustrate the quaternary substituted bleach activators encompassed herein:

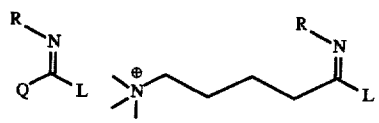

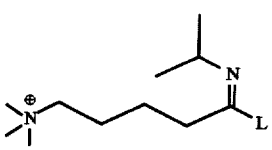

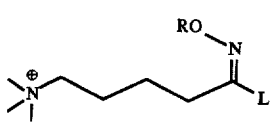

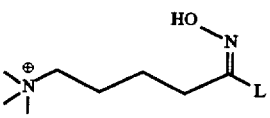

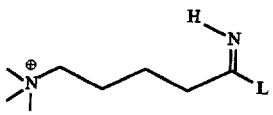

It is understood that

is functionally equivalent to

as further illustrated in the following embodiments:

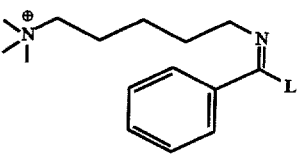

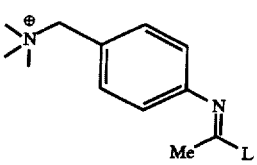

Leaving-groups—The leaving-group, L, in quaternary substituted bleach activators herein are generally selected from the group consisting of cyclic amidines with a ring size of from about 5 to about 12 atoms:

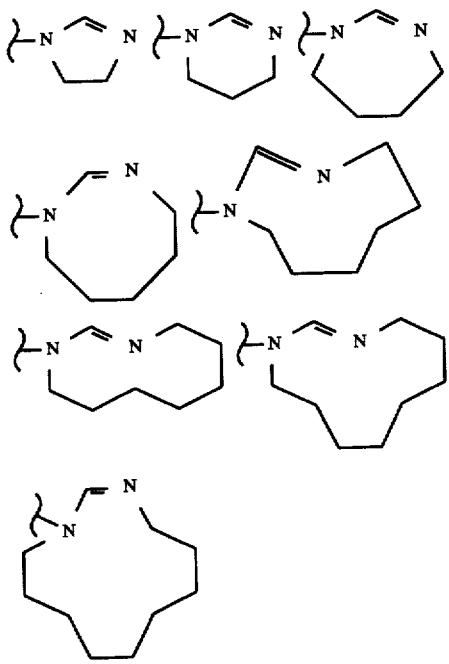

Preferred cyclic amidines have a ring size of from about 5 to about 7 atoms as in the first three of the above structures. The invention also encompasses, by way of L, lactams with a ring size of from about 6 to about 12:

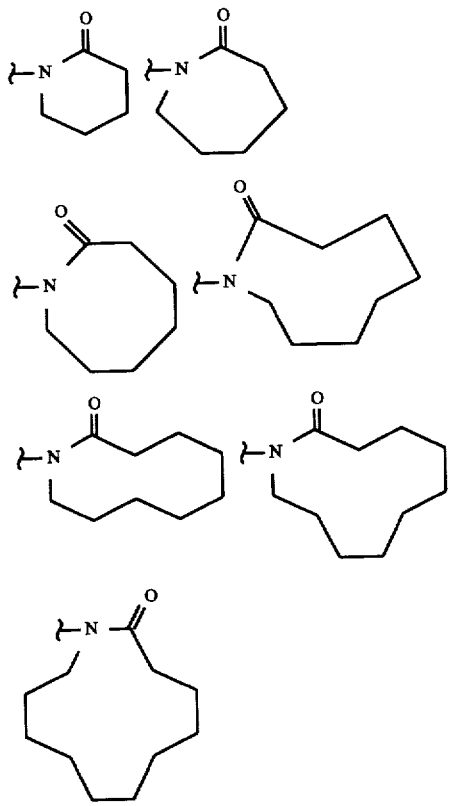

Preferred lactam ring sizes are of from about 6 to about 7 atoms as in the first two of the above structures.

Also, anilino derivatives are within the scope of allowable leaving-groups L herein. Such anilino derivatives are further illustrated as follows:

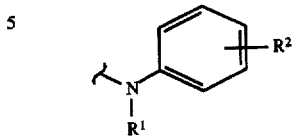

which includes compounds $R^1$ and $R^2$ may be fused, e.g.,

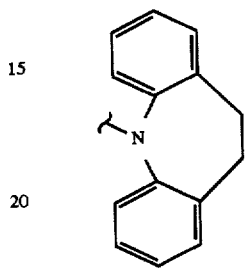

Of course, mixtures of leaving-groups are possible within the same quaternary substituted bleach activator structure, as in:

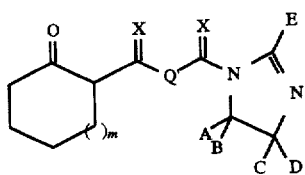

Mixtures of any of the quaternary substituted bleach activators with each other or with conventional bleach activators are quite acceptable for use in the instant bleaching compositions.

In preferred embodiments of the present invention, L is selected from the group consisting of a) 4,5-saturated 5-membered cyclic amidine having the formula:

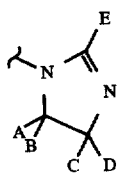

wherein E is selected from the group consisting of H, aryl, substituted aryl, alkaryl, ethoxylated alkyl, substituted alkaryl and linear or branched substituted or unsubstituted alkyl and wherein A, B, C, D are any oxidation resistant substituents; b) caprolactams; c) valerolactams; and d) mixtures thereof.

Moieties Q—Q comprises a tetravalent or cationic (used interchangeably) nitrogen atom $N^{30}$, wherein the nitrogen atom is covalently connected to the moiety —C(X)L by a single, double, or triple aliphatic, aromatic or aliphatic/aromatic linkage. The atom in Q to which moiety —C(X)— is bonded is a carbon atom. Further, when the linkage is aliphatic, the linkage comprises at least two carbon atoms between the tetravalent nitrogen atom and the moiety —C(X)—. Preferred Q's are selected from $R^1R^2R^3N^+T$ wherein $R^1$, $R^2$ and $R^3$ can vary independently. Each R moiety is selected from the group consisting of H, methyl, ethyl, aryl, substituted aryl, alkaryl, substituted alkaryl, ethoxylated alkyl, linear or branched, substituted or unsubstituted, saturated or unsaturated $C_n$ alkyl, wherein n is from 3 to about 16, and mixtures thereof T is selected from the group consisting of —$(CH_2)_i$— wherein i is from about 3 to about 12; —$(CH_2)_i(C_6H_4)(CH_2)_j$— wherein i and j are independently from 0 to about 12 provided that at least one of i and j is nonzero and the polyalkylene substituents attached to $C_6H_4$ are o-, m- or p- to each other; -(Aryl)-; (Alkyl)G(Aryl)-; -(Alkyl)G(Alkyl)-; -(Aryl)G(Alkyl)-; and -(Aryl)G(Aryl)-; wherein G is selected from O, —C(O)N($R^4$)—, —S(O)$_2$N($R^4$)—, —N($R^4$)C(O)—, —N($R^4$)S(O)$_2$—, —S(O)$_2$— and —N($R^4$)C(O)N($R^5$)— wherein $R^4$ and $R^5$ are H or alkyl. Counter-anions—Preferred compositions of this invention comprise charge-balancing compatible anions or "counter-ions". In general, these may be monovalent, divalent, trivalent or polyvalent. Available anions such as bromide, chloride or phosphates may be used, though they may be other than preferred for one or another reason, such as bleach reactivity or phosphorus content. Preferred compatible anions are selected from the group consisting of sulfate, isethionate, alkanesulfonate, alkyl sulfate, aryl sulfonate, alkaryl sulfonate, carboxylates, polycarboxylates, and mixtures thereof. Preferred anions include the sulfonates selected from the group consisting of methanesulfonate, ethanesulfonate, benzenesulfonate, p-toluenesulfonate, cumenesulfonate, xylenesulfonate, naphthalene sulfonate and mixtures thereof Especially preferred of these sulfonates are those which contain aryl. Preferred alkyl sulfates include methyl sulfate and octyl sulfate. Preferred polycarboxylate anions suitable herein are nonlimitingly illustrated by terephthalate, polyacrylate, polymaleate, poly (acrylate-comaleate), or similar polycarboxylates; preferably such polycarboxylates have low molecular weights, e.g., 1,000–4,500. Suitable monocarboxylates are further illustrated by benzoate, naphthoate, p-toluate, and similar hard-water precipitation-resistant monocarboxylates.

Electron-withdrawing substitutents—Bleaching compositions herein may comprise quaternary substituted bleach activators comprising at least one electron-withdrawing or aromatic substituent in Q, such that the $pK_a$ of the peracid form of the QSBA, e.g., QC(X)OOH, is less than the $pK_a$ of the nonsubstituted form. Preferably the electron-withdrawing substituent is neutral. More preferably the electron-withdrawing substituent is nitro, an aromatic moiety having a electron-withdrawing effect, or a combination of the two.

The effects of electron withdrawing substituents on the aqueous $pK_a$ of aliphatic and aromatic peroxy acids are well understood and documented (see W. M. Richardson, in *The Chemistry of the Functional Groups, Peroxides*, Ed. S. Patai, Wiley, New York, 1983, Chapter 5, pp 130,131 and references therein). Without being limited by theory, it is believed that stronger peracids provide enhanced performance.

Surface Activity of QSBA or Peracid—For bleaching compositions such as laundry detergent compositions herein, preferably the quaternary substituted bleach activator is surface-active, having a critical micelle concentration of less than or equal to about $10^{-2}$ molar. Such surface-active activators preferably comprise one long-chain moiety having a chain of from about 8 to about 12 atoms; the counter-ion is preferably non surface-active. The term "surface active" is well-known in the art and characterizes compounds which comprise at least one group with an affinity for the aqueous phase and, typically, a hydrocarbon chain with little affinity for water. Surface active compounds dissolved in a liquid, in particular in water, lower the surface tension or interfacial tension by positive adsorption at the liquid/vapor interface, or the soil-water interface. Critical micelle concentration ($c_m$ or "cmc"): is likewise a regognized term, referring to the characteristic concentration of a surface active material in solution above which the appearance and development of micelles brings about sudden variation in the relation between the concentration and certain physico-chemical properties of the solution. Said physico-chemical properties include density, electrical conductivity, surface tension, osmotic pressure, equivalent electrical conductivity and interfacial tension.

$pK_a$ Rate and Perhydrolysis Criticalities

In accordance with the present invention, there are provided bleaching compositions wherein quaternary substituted bleach activators are required to respect criticalities of $pK_a$ and criticalities relating to rates of perhydrolysis, hydrolysis and diacylperoxide formation. Furthermore, perhydrolysis effciency is important in selecting the quaternary substituted bleach activator. All of these criticalities will be better understood and appreciated in light of the following disclosure.

$pK_a$ Value—The acids in which organic chemists have traditionally been interested span a range, from the weakest acids to the strongest, of about 60 pK units. Because no single solvent is suitable over such a wide range, establishment of comprehensive scales of acidity necessitates the use of several different solvents. Ideally, one might hope to construct a universal acidity scale by relating results obtained in different solvent systems to each other. Primarily because solute-solvent interactions affect acid-base equilibria diffently in different solvents, it has not proven possible to establish such a scale.

Water is taken as the standard solvent for establishing an acidity scale. It is convenient, has a high dielectric constant, and is effective at solving ions. Equilibrium acidities of a host of compounds (e.g., carboxylic acids and phenols) have been determined in water. Compilations of pK data may be found in Perrin, D. D. "Dissociation Constants of Organic Bases in Aqueous Solution"; Butterworths: London, 1965 and Supplement, 1973; Serjeant, E. P.; Dempsey, B. "Ionisation Constants of Organic Acids in Aqueous Solution"; 2nd ed., Pergammon Press: Oxford, 1979. Experimental methods for determining $pK_a$ values are described in the original papers. The $pK_a$ values that fall between 2 and 10 can be used with a great deal of confidence; however, the further removed values are from this range, the greater the degree of skepticism with which they must be viewed.

For acids too strong to be investigated in water solution, more acidic media such as acetic acid or mixtures of water with perchloric or sulfuric acid are commonly employed; for acids too weak to be examined in water, solvents such as liquid ammonia, cyclohexylamine and dimethylsulfoxide have been used. The Hammett $H_o$ acidity function has allowed the aqueous acidity scale, which has a practical $pK_a$ range of about 0–12, to be extended into the region of negative $pK_a$ values by about the same range. The use of $H_{13}$ acidity functions that employ strong bases and cosolvents has similarly extended the range upward by about 12 $pK_a$ units.

The present invention involves the use of leaving groups the conjugate acids of which are considered to be weak; they possess aqueous $pK_a$ values greater than about 13. To establish only that a given compound has an aqueous $pK_a$ above about 13 is straightforward. As noted above, values much above this are difficult to measure with confidence without resorting to the use of an acidity function. While the measurement of the acidity of weak acids using the $H_-$ method has the advantage of an aqueous standard state, it is restricted in that (1) it requires extrapolation across varying solvent media and (2) errors made in determining indicator $pK_a$ values are cumulative. For these and other reasons, Bordwell and co-workers have developed a scale of acidity in dimethylsulfoxide (DMSO), and it is this scale which we use to define the upper limits of $pK_a$ for the conjugate acids of our leaving groups. This solvent has the advantage of a relatively high dielectric constant ($\epsilon=47$); ions are therefore dissociated so that problems of differential ion pairing are reduced. Although the results are referred to a standard state in DMSO instead of in water, a link with the aqueous $pK_a$ scale has been made. When acidities measured in water or on a water-based scale are compared with those measured in DMSO, acids whose conjugate bases have their charge localized are stronger acids in water; acids whose conjugate bases have their charge delocalized over a large area are usually of comparable strength. Bordwell details his findings in a 1988 article (*Acc. Chem. Res.* 1988, 21, 456-463). Procedures for measurement of $pK_a$ in DMSO are found in papers referenced therein.

Definitions of $k_H$, $k_P$, and $k_D$—In the expressions given below, the choice of whether to use the concentration of a nucleophile or of its anion in the rate equation was made as a matter of convenience. One skilled in the art will realize that measurement of solution pH provides a convenient means of directly measuring the concentration of hydroxide ions present. One skilled in the art will further recognize that use of the total concentrations of hydrogen peroxide and peracid provide the most convenient means to determine the rate constants $k_P$ and $k_D$.

The terms, such as RC(O)L, used in the following definitions and in the conditions for the determination of $k_H$, $k_P$ and $k_D$, are illustrative of a general bleach activator structure and are not limiting to any specific quaternary substituted bleach activator structure herein. Specifically, the term "RC(O)L" could be substituted with "QC(O)L" or "QC(X)L", etc.

Definition of $k_H$ $$RC(O)L + HO^- \rightarrow RC(O)O^- + HL$$

The rate of the reaction shown above is given by

Rate=kH[RC(O)L][HO⁻]

The rate constant for hydrolysis of bleach activator ($k_H$) is the second order rate constant for the bimolecular reaction between bleach activator and hydroxide anion as determined under the conditions specified below.

Definition of $k_P$ $$RC(O)L + H_2O_2 \rightarrow RC(O)O_2H + HL$$

The rate of the reaction shown above is given by

Rate=k$_P$[RC(O)L][H$_2$O$_2$]$_T$ where $[H_2O_2]_T$ represents the total concentration of hydrogen peroxide and is equal to $[H_2O_2]+[HO_2^-]$. The rate constant for perhydrolysis of bleach activator ($k_P$) is the second order rate constant for the bimolecular reaction between bleach activator and hydrogen peroxide as determined under the conditions specified below.

Definition of $k_D$ $$RC(O)L + RC(O)O_2H \rightarrow RC(O)O_2C(O)R + HL$$

The rate of the reaction shown above is given by

Rate=k$_D$[RC(O)L][RC(O)O$_2$H]$_T$ where $[RC(O)O_2H]_T$ represents the total concentration of peracid and is equal to $[RC(O)O_2H]+[RC(O)O_2^-]$.

The rate constant for the formation of a diacylperoxide from the bleach activator ($k_D$), the second order rate constant for the bimolecular reaction between bleach activator and peracid anion, is calculated from the above defined $k_D$. The value for $k_D$ is determined under the conditions specified below.

Conditions for the Determination of Rate Constants

Hydrolysis—A set of experiments is completed to measure the rate of hydrolysis of a bleach activator RC(O)L in aqueous solution at total ionic strength of 1M as adjusted by addition of NaCl. The temperature is maintained at 35.0°±0.1° C. and the solution is buffered with NaHCO$_3$+Na$_2$CO$_3$. A solution of the activator ([RC(O)L]=0.5 mM) is reacted with varying concentrations of NaOH under stopped-flow conditions and the rate of reaction is monitored optically. Reactions are run under pseudo first-order conditions to determine the bimolecular rate constant for hydrolysis of bleach activator ($k_H$). Each kinetic run is repeated at least five times with about eight different concentrations of hydroxide anions. All kinetic traces give satisfactory fits to a first-order kinetic rate law and a plot of the observed first-order rate constant versus concentration of hydroxide anion is linear over the region investigated. The slope of this line is the derived second order rate constant $k_H$.

Perhydrolysis—A set of experiments is completed to measure the rate of perhydrolysis of a bleach activator RC(O)L in aqueous solution at pH=10.0 with constant ionic strength of 1M as adjusted by addition of NaCl. The temperature is maintained at 35.0°±0.1° C. and the solution is buffered with NaHCO$_3$+Na$_2$CO$_3$. A solution of the activator ([RC(O)L]=0.5 mM) is reacted with varying concentrations of sodium perborate under stopped-flow conditions and the rate of reaction is monitored optically. Reactions are run under pseudo first-order conditions in order to determine the bimolecular rate constant for perhydrolysis of bleach activator ($k_P$). Each kinetic run is repeated at least five times with about eight different concentrations of sodium perborate. All kinetic traces give satisfactory fits to a first-order kinetic rate law and a plot of the observed first-order rate constant versus total concentration of hydrogen peroxide is linear over the region investigated. The slope of this line is the derived second order rate constant $k_P$. One skilled in the art recognizes that this rate constant is distinct from, but related to, the second order rate constant for the reaction of a bleach activator with the anion of hydrogen peroxide ($k_{nuc}$). The relationship of these rate constants is given by the following equation:

$$k_{nuc}=k_P\{(K_a[H^+])/K_a\}$$

where $K_a$ is the acid dissociation constant for hydrogen peroxide.

Formation of diacylperoxide—A set of experiments is completed to measure the rate of formation of a diacylperoxide RC(O)O$_2$C(O)R from a bleach activator RC(O)L in aqueous solution at pH=10.0 with constant ionic strength of 1M as adjusted by addition of NaCl. The temperature is maintained at 35.0°±0.1° C. and the solution is buffered with NaHCO$_3$+Na$_2$CO$_3$. A solution of the activator ([RC(O)L]= 0.5 mM) is reacted with varying concentrations of peracid under stopped-flow conditions and the rate of reaction is monitored optically. Reactions are run under pseudo first-order conditions in order to determine the bimolecular rate constant $k_{D'}$. Each kinetic run is repeated at least five times with about eight different concentrations of peracid anion. All kinetic traces give satisfactory fits to a first-order kinetic rate law and a plot of the observed first-order rate constant versus total concentration of peracid is linear over the region investigated. The slope of this line is the derived second order rate constant $k_{D'}$. The bimolecular rate constant for the formation of a diacylperoxide from peracid anion ($k_D$) is calculated according to $$k_D = k_{D'}\{(K_a + [H^+])/K_a\}$$

where $K_a$ is the acid dissociation constant for the peracid $RC(O)O_2H$. One skilled in the art will realize that the $pK_a$ values for peracids fall into a rather narrow range from about 7 to about 8.5 and that at pH=10.0, when $K_a \geq$ about $10^{-8}$, $\{(K_a + [H^+])/K_a\} \cong 1$ and $k_D \cong k_{D'}$.

Test for Perhydrolysis Efficiency—This method is applicable as a test for screening any bleach activators RC(O)L (not intending to be limiting of any specific quaternary substituted bleach activator structure herein) by confirmation of the formation of peracid analyte $RC(O)O_2H$. The minimum standard for perhydrolysis efficiency (PE) is the generation of $\geq 10\%$, preferably $\geq 20\%$, of theoretical peracid within 10 mixtures when tested under the conditions specified below.

Test Conditions—Distilled, deionized water at 40° C. adjusted to pH=10.3 with $Na_2CO_3$, 100 ppm bleach activator RC(O)L, 500 ppm sodium percarbonate Test Protocol—Distilled, deionized water (90 mL; pH adjusted to 10.3 with $Na_2CO_3$) is added to a 150 mL beaker and heated to 40°±1° C. Fifty (50) mg sodium percarbonate is added to the beaker and the mixture is stirred two mixtures before a 10 mL solution containing 10 mg of bleach activator (predissolved in 1 mL of a water miscible organic solvent (e.g., methanol or dimethylformamide) and brought to volume with pH 10.3 distilled, deionized water) is added. The initial time point is taken 1 minute thereafter. A second sample is removed at 10 mixtures. Sample aliquots (2 mL) are examined via analytical HPLC for the quantitative determination of peracid $RC(O)O_2H$.

Sample aliquots are individually mixed with 2 mL of a pre-chilled 5° C. solution of acetonitrile/acetic acid (86/14) and placed in temperature controlled 5° C. autosampler for subsequent injection onto the HPLC column.

High performance liquid chromatography of the authentic peracid under a given set of conditions establishes the characteristic retention time ($t_R$) for the analyte. Conditions for the chromatography will vary depending on the peracid of interest and should be chosen so as to allow baseline separation of the peracid from other analytes. A standard calibration curve (peak area vs. concentration) is constructed using the peracid of interest. The analyte peak area of the 10 minute sample from the above described test is thereby converted to ppm peracid generated for determination of the quantity PE. A bleach activator is considered acceptable when a value of PE=[(ppm of peracid generated)/(theoretical ppm peracid)]×100% $\geq 10\%$ is achieved within ten mixtures under the specified test conditions.

Note, by comparison with 4,5-saturated cyclic amidine embodiments of the instant bleach activators, known closely related chemical compounds wherein the 4,5 position is unsaturated have surprisingly greater rates of hydrolysis. Specifically, acetyl imidazole has $k_H$ greater than $10.0 M^{-1} s^{-1}$. Accordingly this invention does not encompass imidazole as a leaving group.

Bleaching Compositions—The quaternary substituted bleach activators herein are not preferably employed alone but in combination with a source of hydrogen peroxide, as disclosed hereinafter. Levels of the quaternary substituted bleach activators herein may vary widely, e.g., from about 0.05% to about 95%, by weight, of composition, although lower levels, e.g., from about 0.1% to about 20% are more typically used.

Source of hydrogen peroxide—A source of hydrogen peroxide herein is any convenient compound or mixture which under consumer use conditions provides an effective amount of hydrogen peroxide. Levels may vary widely and are typically from about 0.5% to about 60%, more typically from about 0.5% to about 25%, by weight of the bleaching compositions herein.

The source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

While effective bleaching compositions herein may comprise only the quaternary substituted bleach activators of the invention and a source of hydrogen peroxide, fully-formulated laundry and automatic dishwashing compositions typically will also comprise other adjunct ingredients to improve or modify performance. Typical, non-limiting examples of such ingredients are disclosed hereinafter for the convenience of the formulator.

Adjunct Ingredients

Bleach catalysts—If desired, the bleaches can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. App. Pub. Nos. 549,271A1, 549,272A1, 544,440A2., and 544,490A1; Preferred examples of these catalysts include $Mn^{IV}_2(u-O)_3(1,4,7\text{-trimethyl-}1,4,7\text{-triazacyclononane})_2(PF_6)_2$, $Mn^{III}_2(u-O)_1(u-O)_2$ $(1,4,7\text{-trimethyl-}1,4,7\text{-triazacyclononane})_2\text{-}(ClO_4)_2$, $Mn^{IV}_4(u-O)_6(1,4,7\text{-triazacyclononane})_4(ClO_4)_4$, $Mn^{III}Mn^{IV}_4(u-O)_1(u-OAc)_2\text{-}(1,4,7\text{-trimethyl-}1,4,7\text{-triazacyclo-nonane})_2\text{-}(ClO_4)_3$, $Mn^{IV}\text{-}(1,4,7\text{-trimethyl-}1,4,7\text{-triazacyclo-nonane})\text{-}(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. (See U.S. application Ser. No. 08/210,186, filed Mar. 17, 1994.) Other preferred transition metals in said transition-metal-containing bleach catalysts include iron or copper.

As a practical matter, and not by way of limitation, the bleaching compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Conventional Bleach Activators—"Conventional bleach activators" herein are any bleach activators which do not respect the above-identified provisions given in connection with the QSBAs. Numerous conventional bleach activators are known and are optionally included in the instant bleaching compositions. Various nonlimiting examples of such activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylenediamine (TAED) activators are typical, and mixtures thereof can also be used. See also U.S. Pat No. 4,634,551 for other typical conventional bleach activators. Known amido-derived bleach activators are those of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of optional, conventional bleach activators of the above formulae include (6-octanamido-caproyl)oxybenzenesulfonate, (6-nonanamidocaproyl)oxybenzenesulfonate, (6-decanamido-caproyl)oxybenzenesulfonate, and mixtures thereof as described in U.S. Pat. No. 4,634,551. Another class of conventional bleach activators comprises the benzoxazin-type activators disclosed by Hodge et al in U.S. Pat. No. 4,966,723, issued Oct. 30, 1990. Still another class of conventional bleach activators includes those acyl lactam activators which do not contain any cationic moiety, such as acyl caprolactams and acyl valerolactams of the formulae $R^6C(O)L^1$ and $R^6C(O)L^2$ wherein $R^6$ is H, an alkyl, aryl, alkoxyaryl, or alkaryl group containing from 1 to about 12 carbon atoms, or a substituted phenyl group containing from 6 to about 18 carbons and wherein $L^1$ and $L^2$ are caprolactam or valerolactam moieties. See copending U.S. applications Ser. No. 08/064,562 and 08/082,270, which disclose substituted benzoyl lactams. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, which discloses acyl caprolactams, including benzoyl caprolactam, adsorbed into sodium perborate.

Bleaching agents other than hydrogen peroxide sources are also known in the art and can be utilized herein as adjunct ingredients. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonated zinc phthalocyanine.

Organic Peroxides, especially Diacyl Peroxides—are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88–57, incorporated by reference. Preferred diacyl peroxides herein whether in pure or formulated form for granule, powder or tablet forms of the bleaching compositions constitute solids at 25° C., e.g., CADET® BPO 78 powder form of dibenzoyl peroxide, from Akzo. Highly preferred organic peroxides, particularly the diacyl peroxides, for such bleaching compositions have melting points above 40° C., preferably above 50° C. Additionally, preferred are the organic peroxides with SADT's (as defined in the foregoing Akzo publication) of 35° C. or higher, more preferably 70° C. or higher. Non-limiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate. In general, particularly for automatic dishwashing applications, it is preferred to use diacyl peroxides which are substantially free from oily phthalates since these can form smears on dishes and glassware.

Conventional Quaternary Substituted Bleach Activators—The present compositions can optionally further comprise conventional, known quaternary substituted bleach activators (CQSBA). CQSBA's are further illustrated in U.S. Pat. No. 4,539,130, Sep. 3, 1985 and U.S. Pat. No. 4,283,301. British Pat. 1,382,594, published Feb. 5, 1975, discloses a class of CQSBA's optionally suitable for use herein. U.S. Pat. No. 4,818,426 issued Apr. 4., 1989 discloses another class of CQSBA's. Also see U.S. Pat. No. 5,093,022 issued Mar. 3, 1992 and U.S. Pat No. 4,904,406, issued Feb. 27, 1990. Additionally, CQSBA's are described in EP 552,812 A1 published Jul. 28, 1993, and in EP 540,090 A2, published May 5, 1993. Particularly preferred are CQSBA's having a caprolactam or valerolactam leaving group, and are the subject of copending applications, in particular co-pending commonly assigned British Patent Appl. Ser. No. 9407944.9, filed Apr. 21, 1994, P&G Case No. CM705F.

Detersive Surfactants—Nonlimiting examples of surfactants useful herein include the conventional $C_{11}$–$C_{18}$ alkylbenzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3-M^+)CH_3$ and $CH_3(CH_2)_y(CHOSO_3-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("AE$_x$S"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxylate/propoxylates), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Automatic dishwashing compositions typically employ low sudsing surfactants, such as the mixed ethyleneoxy/propyleneoxy nonionics. Other conventional useful surfactants are listed in standard texts.

Builders—Detergent builders can optionally be included in the compositions herein to assist in controlling mineral hardness. Inorganic as well as organic builders can be used. Builders are typically used in automatic dishwashing and fabric laundering compositions to assist in the removal of particulate soils.

The level of builder can vary widely depending upon the end use of the composition and its desired physical form. When present, the compositions will typically comprise at least about 1% builder. High performance compositions typically comprise from about 10% to about 80%, more typically from about 15% to about 50% by weight, of the detergent builder. Lower or higher levels of builder, however, are not excluded.

Inorganic or P-containing detergent builders include, but are not limited to, the alkaryl metal, ammonium and alkanolammonium salts of polyphosphates (exemplified by the tripolyphosphates, pyrophosphates, and glassy polymeric metephosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders. See U.S. Pat. No. 4,605,509 for examples of preferred aluminosilicates.

Examples of silicate builders are the alkaryl metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6® is a crystalline layered silicate marketed by Hoechst (commonly abbreviated herein as "SKS-6"). Unlike zeolite builders, the Na SKS-6 silicate builder does not contain aluminum. NaSKS-6 is the $\delta$-$Na_2SiO_5$ morphology form of layered silicate and can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the $\alpha$-, $\beta$- and $\gamma$-forms. Other silicates may also be useful, such as for example magnesium silicate, which can serve as a crispening agent in granular formulations, as a stabilizing agent for oxygen bleaches, and as a component of suds control systems.

Silicates useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Examples of carbonate builders are the alkaline earth and alkaryl metal carbonates as disclosed in German Patent Application No. 2,321,001 published on Nov. 15, 1973. Various grades and types of sodium carbonate and sodium sesquicarbonate may be used, certain of which are particularly useful as carriers for other ingredients, especially detersive surfactants.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula: $[M_z(zAlO_2)_y] \cdot xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite & Zeolite P (B), Zeolite MAP and Zeolite X. In an especially preferred embodiment, the crystalline aluminosilicate ion exchange material has the formula: $Na_{12}[(AlO_2)_{12}(SiO_2)_{12}] \cdot xH_2O$ wherein x is from about 20 to about 30, especially about 27. This material is known as Zeolite A. Dehydrated zeolites (x=0 –10) may also be used herein. Preferably, the aluminosilicate has a particle size of about 0.1–10 microns in diameter. As with other builders such as carbonates, it may be desirable to use zeolites in any physical or morphological form adapted to promote surfactant carrier function, and appropriate particle sizes may be freely selected by the formulator.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et at, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5- tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty laundry detergent formulations due to their availability from renewable resources and their biodegradability. Citrates can also be used in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0.200.263, published Nov. 5, 1986.

Other suitable polycarboxylates are disclosed in U.S. Pat. No. 4,144,226, Crutchfield et at, issued Mar. 13, 1979 and in U.S. Pat. No. 3,308,067, Diehl, issued Mar. 7, 1967. See also U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Chelating Agents—The compositions herein may also optionally contain one or more iron and/or manganese chelating agents, such as hydroxyethyldiphosphonate (HEDP). More generally, chelating agents suitable for use herein can be selected from the group consisting of aminocarboxylates, aminophosphonates, polyfunctionally-substituted aromatic chelating agents and mixtures thereof. Without intending to be bound by theory, it is believed that the benefit of these materials is due in part to their exceptional ability to remove iron and manganese ions from washing solutions by formation of soluble chelates; other benefits include inorganic film or scale prevention. Other suitable chelating agents for use herein are the commercial DEQUEST® series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts therein and mixtures therein.

Aminophosphonates are also suitable for use as chelating agents in the compositions of the invention when at least low levels of total phosphorus are permitted in detergent compositions, and include ethylenediaminetetrakis (methylenephosphonates). Preferably, these aminophosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as Magnesium salts, may also be useful.

If utilized, especially in ADD compositions, these chelating agents or transition-metal-selective sequestrants will preferably comprise from about 0.001% to about 10%, more preferably from about 0.05% to about 1% by weight of the bleaching compositions herein.

Enzymes—Enzymes can be included in the formulations herein for a wide variety of fabric laundering or other cleaning purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of B. subtilis and B. licheniformis. Another suitable protease is obtained from a strain of Bacillus, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et at, published Jan. 9, 1985).

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76 in combination with one or more amino acid residue positions equivalent to those selected from the group consisting of +99, +101, +103, +107 and +123 in *Bacillus amyloliquefaciens* subtilisin as described in the patent applications of A. Baeck, C. K. Ghosh, P. P. Greycar, R. R. Bolt and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626.

Amylases include, for example, α-amylases described in British Patent Specification No. 1,296,839 (Novo), RAPIDASE®, International Bio-Synthetics, Inc. and TERMAMYL®, Novo Industries.

Cellulases usable in the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6 , 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247.832. CAREZYME® (Novo) is especially useful.

Suitable lipase enzymes for detergent use include those produced by microorganisms of the Pseudomonas group, such as *Pseudomonas stutzeri* ATCC 19,154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. lipolyticum NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

Peroxidase enzymes can be used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et at, and European Patent Application Publication No. 0 199 405, Application No. 86200586.5, published Oct. 29, 1986, Venegas. Enzyme stabilization systems are also described, for example, in U.S. Pat. No. 3,519,570.

Other Ingredients—Usual detersive ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Adjuncts which can also be included in detergent compositions employed in the present invention, in their conventional art-established levels for use (generally from 0% to about 20% of the detergent ingredients, preferably from about 0.5% to about 10%), include other active ingredients such as dispersant polymers from BASF Corp. or Rohm & Haas; color speckles, anti-tarnish and/or anti-corrosion agents, dyes, fillers, optical brighteners, germicides, alkalinity sources, hydrotropes, anti-oxidants, enzyme stabilizing agents, perfumes, solubilizing agents, clay soil removal/anti-redeposition agents, carriers, processing aids, pigments, solvents for liquid formulations, fabric softeners, static control agents, solid fillers for bar compositions, etc. Dye transfer inhibiting agents, including polyamine N-oxides such as polyvinylpyridine N-oxide can be used. Dye-transfer-inhibiting agents are further illustrated by polyvinylpyrrolidone and copolymers of N-vinyl imidazole and N-vinyl pyrrolidone. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT® D10, Degussa) is admixed with a proteolytic enzyme solution containing 3%–5% of $C_{13-15}$ ethoxylated alcohol (EO 7) nonionic surfactant. Typically, the enzyme/surfactant solution is 2.5 X the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid or gel compositions can contain some water and other fluids as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

Certain bleaching compositions herein among the generally encompassed liquid (easily flowable or gel forms) and solid (powder, granule or tablet) forms, especially bleach additive compositions and hard surface cleaning compositions, may preferably be formulated such that the pH is acidic during storage and alkaline during use in aqueous cleaning operations, i.e., the wash water will have a pH in the range from about 7 to about 11.5. Laundry and automatic dishwashing products are typically at pH 7–12, preferably 9 to 11.5. Automatic dishwashing compositions, other than rinse aids which may be acidic, will typically have an aqueous solution pH greater than 7. Techniques for controlling pH at recommended usage levels include the use of buffers, alkalis, acids, pH-jump systems, dual compartment containers, etc., and are well known to those skilled in the art. The compositions are useful from about 5° C. to the boil for a variety of cleaning and bleaching operations.

Bleaching compositions in granular form typically limit water content, for example to less than about 7% free water, for best storage stability. Storage stability of bleach compositions can be further enhanced by limiting the content in the compositions of adventitious redox-active substances such as rust and other traces of transition metals in undesirable form. Certain bleaching compositions may moreover be limited in their total halide ion content, or may have any particular halide, e.g., bromide, substantially absent. Bleach stabilizers such as stannates can be added for improved stability and liquid formulations may be substantially nonaqueous if desired.

The following examples illustrate the QSBA's of the invention, intermediates for making same and bleaching compositions which can be prepared using the QSBA's, but are not intended to be limiting thereof.

EXAMPLE I

PREPARATION OF N-[4-(TRIETHYLAMMONIOMETHYL)BENZOYL] CAPROLACTAM, CHLORIDE SALT 4-chloromethyl benzoyl acid chloride—A 1-neck round bottom flask is fitted with an addition funnel, gas inlet and magnetic stirring and charged with 4-chloromethyl benzoic acid (0.5 mol), toluene (1.0 mol acid/350 ml) and a boiling stone under Argon. Thionyl chloride (1.0 mol) is added dropwise via an addition funnel. A reflux condenser is substituted for the additional funnel and the reaction is heated to toluene reflux for 4 hours under Argon. The reaction is cooled to room temperature. The solvent is evaporated.

4-chloromethyl benzoyl caprolactam—A 3-neck round bottom flask is fitted with mechanical stirring, reflux condenser, addition funnel, and gas inlet and is charged with caprolactam (0.5 mol), triethylamine (0.75 mol) and 75% of the required toluene (1.0 mol caprolactam/1.5 liters) under Argon. The solution is heated to toluene reflux. 4-chloromethyl benzoyl acid chloride (0.5 mol) suspended in remaining toluene is added in a slow stream. The reaction is stirred under Argon at toluene reflux for 6 hours, cooled slightly and filtered. The collected solids, triethylamine hydrochloride, is discarded and the filtrate is refrigerated to precipitate product. The product is collected by vacuum filtration, washed and dried.

N-[4-(triethylammoniomethyl)benzoyl]caprolactam, chloride salt—A 1-neck round bottom flask is fitted with magnetic stirring, addition funnel and gas inlet and is charged with 4-chloromethyl benzoyl caprolactam (0.5 mol) and acetonitrile (1 mole caprolactam/1.5 liters) under Argon. Triethylamine (1.0 mol) is added dropwise. A reflux condenser is substituted for the addition funnel and the reaction is heated to acetonitrile reflux for 4 hours under Argon. The reaction is cooled to room temperature and solvent is evaporated. Excess acetone is added to the flask with magnetic stirring to break apart the product. The mixture is heated to acetone reflux briefly then cooled to room temperature. The product, a QSBA, is vacuum filtered, washed and dried.

The synthesis of Example I may be repeated, but with substitution of valerolactam for caprolactam. The synthesis may also be repeated with, for example, the substitution of trimethylamine for triethylamine. In each instance, the corresponding QSBA is secured.

EXAMPLE II

PREPARATION OF 6-(N,N,N-TRIMETHYLAMMONIO)HEXANOYL CAPROLACTAM p-TOLUENESULFONATE (COMPOUND 5)

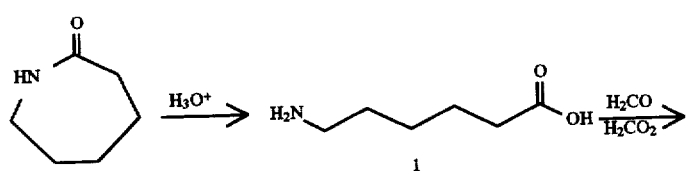

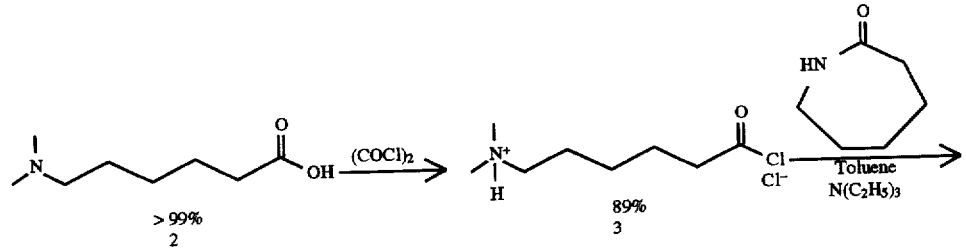

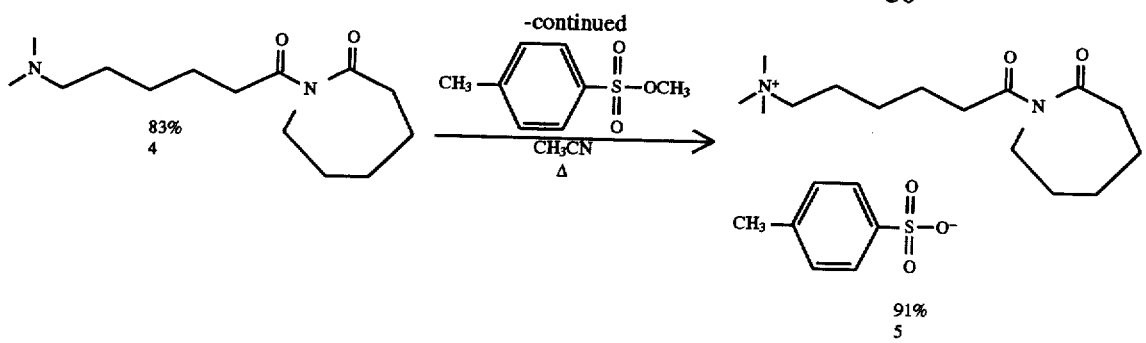

6-(N,N-Dimethylamino)hexanoic acid (2) To a 2000 g three-necked round-bottomed flask equipped with an internal thermometer and reflux condenser are added 6-aminocaproic acid (200.00 g, 1.53 mol), formaldehyde (357.61 g, 4.41 mol, 37 wt %), and formic acid (454.56 g, 8.69 mol, 88%). Once addition is complete, the mixture is heated to reflux for 3 h, then cooled to room temperature. Analysis by TLC (74:25:1, propanol:water:formic acid, $R_f$=0.45) indicates the reaction is complete. To the crude mixture is added 158 g of concentrated HCl (36–37%). The mixture is concentrated to dryness by rotary evaporation for 5 h to remove excess formaldehyde and formic acid. The hydrochloride is redissolved in 300 g of water and neutralized with 132.5 g of 50 wt % NaOH solution to a pH of about 7.0. The mixture is concentrated by rotary evaporation with isopropanol to facilitate drying. The product is leached out from the solids by triturating with dichloromethane. After drying the organic layer over $MgSO_4$ and filtering, the product is isolated by concentrating the organic layer by rotary evaporation and drying under vacuum to give 2 as a white solid, 251.86 g (>99% yield): mp 89°–91° C. ($H_2O$).

6-(N,N-Dimethylamino)hexanoyl chloride hydrochloride (3) Into a 500 mL three-necked round-bottomed flask equipped with a reflux condenser, internal thermometer, mechanical stirrer, and argon inlet, is placed oxalyl chloride (398.67 g, 3.14 mol). Acid 2 (100 g, 0.63 moo is added over 30 min while maintaining the reaction temperature at 40° C. As reaction takes place, $CO_2$ and CO are swept away from the mixture with argon. After addition is complete, the mixture is stirred for 2 h while the reaction flask cools to room temperature. Excess oxalyl chloride is removed by rotary evaporation at 50° C. and then by Kugelrohr distillation at 50° C. (0.1 mm Hg) for 2 h. Isolated is 3, 118.98 g (88.5%) as an oil that solidifies on standing.

6-(N,N-Dimethylamino)hexanoyl caprolactam (4) To a 1000 mL three-necked round-bottomed flask equipped with a reflux condenser, internal thermometer, argon inlet, and mechanical stirrer, are added ε-caprolactam (48.04 g, 0.42 mol), toluene (340 mL), and triethylamine (189.00 g, 1.87 mol). The mixture is heated to reflux (ca. 101° C.) for 15 min. While at that temperature, acid chloride 3 (100.00 g, 0.47 mol) is added as a solid over 30 min. The reaction is maintained at reflux for an additional 1.75 h before the heat is removed. At room temperature, the mixture is filtered and the salts washed with toluene. The dark filtrate is washed with saturated sodium bicarbonate solution (3×250 mL), water (100 mL), and dried over $MgSO_4$. The mixture is filtered and concentrated by rotary evaporation at about 50° C. (water aspirator) and then by Kugelrohr distillation at 60° C. for 1 h to give 89.64 g (83%) of 4 as an oil; bp 80°–85° C. (0.05 mm Hg).

6-(N,N,N-Trimethylammonio)hexanoyl caprolactam p-toluenesulfonate (5) In a 500 mL three-necked round-bottomed flask fitted with an argon inlet, condenser, and stir bar are placed amine amide 4 (17.94 g, 0.071 mol), acetonitrile (200 mL), and methyl p-toluenesulfonate (13.13 g, 0.071 mol). While adding the tosylate, the reaction mixture mildly exotherms. The mixture is heated to reflux for 3 h and is then cooled to room temperature. While concentrating the mixture by rotary evaporation, a tan solid forms which is re-dissolved in a minimal amount of acetonitrile and triturated with ether until a free flowing dispersion of the solid is obtained in the solvent system. The solid is collected by vacuum filtration under a blanket of nitrogen and transferred to a round-bottomed flask. The solid product is dried at room temperature under vacuum (0.1 mmHg) for 24 h to give 5 (27.84 g, 90%) as an off-white solid, mp 128°–131° C. (softens at 118° C.).

EXAMPLE III 6-(N,N,N-TRIMETHYLAMMONIO)HEXANOYL 2-METHYL-2-IMIDAZOLINE p-TOLUENESULFONATE

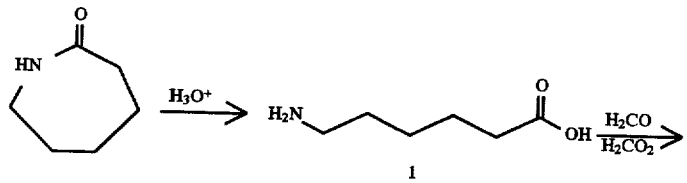

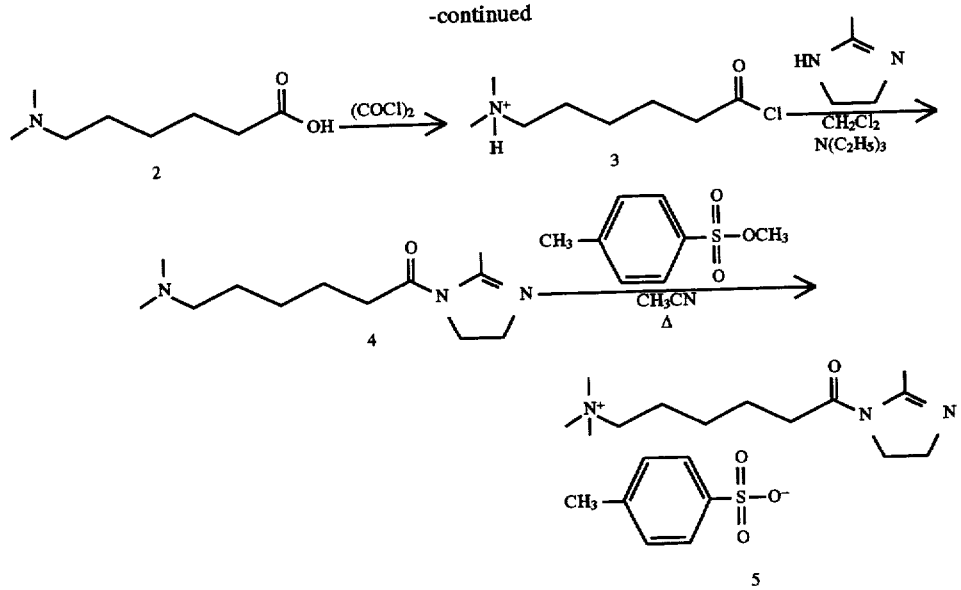

6-(N,N-Dimethylamino)hexanoyl 2-methyl-2-imidazoline (4). Dichloromethane (400 mL), 2-methyl-2-imidazoline (56.38 g, 0.637 mol), and triethylamine (283.51 g, 2.802 mol) are placed in a 2000 mL three-necked round bottomed flask equipped with a reflux condenser, internal thermometer, mechanical stirrer, addition funnel, and argon inlet. The solution is brought to reflux and 15 min later a solution of 6-(N,N-Dimethylamino)hexanoyl chloride.hydrochloride (150 g, 0.700 mol), prepared as described in example II, dissolved in dichloromethane (300 mL) is added dropwise over 45 min. The mixture is refluxed for an additional 2 h before being cooled to room temperature. The salts are filtered and washed with methylene chloride. The combined filtrates are washed with 5% NaHCO$_3$ solution (3×300 mL) and water (300 mL). After drying over MgSO$_4$ and filtration, the organic layer is concentrated first by rotary evaporation at 50° C. and then by Kugelrohr distillation at 60°–70° C. (0.2 mm Hg) to give 95.20 g (66%) of an oil which solidifies on standing.

6-(N,N,N-Trimethylammonio)hexanoyl 2-methyl-2-imidazoline p-toluenesulfonate (5). 6-(N,N-Dimethylamino)hexanoyl 2-methyl-2-imidazoline (50.00 g, 0.222 mol), acetonitrile (150 mL), and methyl p-toluenesulfonate (41.32 g, 0.222 mol) are combined in a 500 mL three-necked round-bottomed flask equipped with reflux condenser, argon inlet, and magnetic stirrer. The mixture is heated for 1.3 h, cooled to room temperature, and concentrated by rotary evaporation at 50° C. to give a gold-brown solid. Drying at room temperature at 0.2 mm Hg for 18 h affords the title QSBA, 91.41 g as a solid.

EXAMPLE IV

Examples of other QSBA's of the general formula $R^1R^2R^3N^+TC(O)L\ X^-$ include:

| EXAMPLE IV | R$_1$ | R$_2$ | R$_3$ | L | X- | T |
|---|---|---|---|---|---|---|
| A | CH$_3$CH$_2$ | CH$_3$CH$_2$ | CH$_3$CH$_2$ | CL | Cl- | p-CH$_2$(C$_6$H$_4$) |
| B | CH$_3$ | CH$_3$ | CH$_3$ | CL | Ms | p-C$_6$H$_4$ |
| C | Bz | CH$_3$ | CH$_3$ | CL | Cl- | p-CH$_2$(C$_6$H$_4$) |
| D | CH$_3$(CH$_2$)$_{11}$ | CH$_3$ | CH$_3$ | CL | Ms | p-C$_6$H$_4$ |
| E | CH$_3$(CH$_2$)$_{11}$ | CH$_3$(CH$_2$)$_{11}$ | CH$_3$ | CL | Cl- | o-C$_6$H$_4$ |
| F | CH$_3$(CH$_2$)$_{11}$ | Bz | CH$_3$ | CL | Ms | m-C$_6$H$_4$ |
| G | Np | CH$_3$ | CH$_3$ | CL | Cl- | p-(CH$_2$)$_4$(C$_6$H$_4$) |
| H | CH$_3$ | CH$_3$ | CH$_3$ | CL | Ms | p-C$_6$H$_4$ |
| I | CH$_3$ | CH$_3$ | CH$_3$ | CL | pTs | p-CH$_2$(C$_6$H$_4$) |
| J | CH$_3$ | CH$_3$ | CH$_3$ | CL | Cl- | p-CH$_2$(C$_6$H$_4$) |
| K | CH$_3$(CH$_2$)$_7$ | CH$_3$ | CH$_3$ | CL | Ms | p-CH$_2$(C$_6$H$_4$) |
| L | CH$_3$(CH$_2$)$_7$ | CH$_3$(CH$_2$)$_7$ | CH$_3$ | CL | pTs | p-CH$_2$(C$_6$H$_4$)) |
| M | CH$_3$CH$_2$ | CH$_3$CH$_2$ | CH$_3$CH$_2$ | CL | Cs | p-CH$_2$(C$_6$H$_4$) |
| N | CH$_3$CH$_2$ | CH$_3$CH$_2$ | CH$_3$CH$_2$ | CL | Xs | p-CH$_2$(C$_6$H$_4$) |
| O | CH$_3$CH$_2$ | CH$_3$CH$_2$ | CH$_3$CH$_2$ | CL | Ns | p-CH$_2$(C$_6$H$_4$) |
| P | CH$_3$ | CH$_3$ | CH$_3$ | CL | pTs | CH$_2$CH$_2$NHC(O)m-(C$_6$H$_4$) |
| Q | CH$_3$ | CH$_3$ | CH$_3$ | CL | pTs | CH$_2$CH$_2$O o-(C$_6$H$_4$) | wherein Bz is benzoyl, CL is caprolactam, Np is 1-naphthylmethylene or 2-naphthylmethylene, Ms is methyl sulfonate, pTs is p-toluene sulfonate, Cs is cumenesulfonate, Xs is xylene sulfonate, Ns is 1-naphthyl sulfonate.

EXAMPLE V

Examples of other QSBA's of the general formula $R^1R^2R^3N^+TC(O)L\ X^-$ include:

| EXAMPLE V | $R_1$ | $R_2$ | $R_3$ | L | X- | T |
|---|---|---|---|---|---|---|
| A | $CH_3CH_2$ | $CH_3CH_2$ | $CH_3CH_2$ | IZ | Cl- | $p\text{-}CH_2(C_6H_4)$ |
| B | $CH_3$ | $CH_3$ | $CH_3$ | IZ | Ms | $p\text{-}C_6H_4$ |
| C | Bz | $CH_3$ | $CH_3$ | IZ | Cl- | $p\text{-}CH_2(C_6H_4)$ |
| D | $CH_3(CH_2)_{11}$ | $CH_3$ | $CH_3$ | IZ | Ms | $p\text{-}C6H_4$ |
| E | $CH_3(CH_2)_{11}$ | $CH_3(CH_2)_{11}$ | $CH_3$ | IZ | Cl- | $o\text{-}C_6H_4$ |
| F | $CH_3(CH_2)_{11}$ | Bz | $CH_3$ | IZ | Ms | $m\text{-}C_6H_4$ |
| G | Np | $CH_3$ | $CH_3$ | IZ | Cl- | $p\text{-}(CH_2)_4(C_6H_4)$ |
| H | $CH_3$ | $CH_3$ | $CH_3$ | IZ | Ms | $p\text{-}C_6H_4$ |
| I | $CH_3$ | $CH_3$ | $CH_3$ | IZ | pTs | $p\text{-}CH_2(C_6H_4)$ |
| J | $CH_3$ | $CH_3$ | $CH_3$ | IZ | Cl- | $p\text{-}CH_2(C_6H_4)$ |
| K | $CH_3(CH_2)_7$ | $CH_3$ | $CH_3$ | IZ | Ms | $p\text{-}CH_2(C_6H_4)$ |
| L | $CH_3(CH_2)_7$ | $CH_3(CH)_7$ | $CH_3$ | IZ | pTs | $p\text{-}CH_2(C_6H_4)$ |
| M | $CH_3CH_2$ | $CH_3CH_2$ | $CH_3CH_2$ | IZ | Cs | $p\text{-}CH_2(C_6H_4)$ |
| N | $CH_3CH_2$ | $CH_3CH_2$ | $CH_3CH_2$ | IZ | Xs | $p\text{-}CH_2(C_6H_4)$ |
| O | $CH_3CH_2$ | $CH_3CH_2$ | $CH_3CH_2$ | IZ | Ns | $p\text{-}CH_2(C_6H_4)$ |
| P | $CH_3$ | $CH_3$ | $CH_3$ | IZ | pTs | $CH_2CH_2NHC(O)m\text{-}(C_6H_4)$ |
| Q | $CH_3$ | $CH_3$ | $CH_3$ | IZ | pTs | $CH_2CH_2O\ o\text{-}(C_6H_4)$ | wherein Bz is benzoyl, Iz is 4,5-dihydro-2-methyl-1H-imidazole, Np is 1-naphthylmethylene or 2-naphthylmethylene, Ms is methyl sulfonate, pTs is p-toluene sulfonate, Cs is cumenesulfonate, Xs is xylene sulfonate, Ns is 1-naphthyl sulfonate.

EXAMPLE VI

Granular laundry detergents are exemplified by the following formulations.

| EXAMPLE VI INGREDIENT | A % | B % | C % | D % | E % |
|---|---|---|---|---|---|
| Quaternary Substituted Bleach Activator* | 5 | 5 | 3 | 3 | 8 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylenediamine | 0 | 0 | 0 | 3 | 0 |
| Nonanoyloxybenzenesulfonate | 0 | 0 | 3 | 0 | 0 |
| Linear alkylbenzenesulfonate | 7 | 11 | 19 | 12 | 8 |
| Alkyl ethoxylate (C45E7) | 4 | 0 | 3 | 4 | 6 |
| Zeolite A | 20 | 20 | 7 | 17 | 21 |
| SKS-6® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta(methylene phoshonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethylcellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| Carezyme | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Carbonate | 16 | 14 | 24 | 6 | 23 |
| Silicate | 3.0 | 0.6 | 12.5 | 0 | 0.6 |
| Sulfate, Water, Perfume, Colorants | to 100 | to 100 | to 100 | to 100 | to 100 |

*Quaternary substituted bleach activator according to any of Examples I to V

Additional granular laundry detergents are exemplified by the following formulations.

| EXAMPLE VI INGREDIENT | F % | G % | H % | I % |
|---|---|---|---|---|
| Quaternary Substituted Bleach Activator* | 5 | 3 | 6 | 4.5 |
| Sodium Percarbonate | 20 | 21 | 21 | 21 |
| Tetraacetylethylenediamine | 0 | 6 | 0 | 0 |
| Nonanoyloxybenzenesulfonate | 4.5 | 0 | 0 | 4.5 |
| Alkyl ethoxylate (C45E7) | 2 | 5 | 5 | 5 |
| N-cocoyl N-methyl glucamine | 0 | 4 | 5 | 5 |
| Zeolite A | 6 | 5 | 7 | 7 |
| SKS-6 ® silicate (Hoechst) | 12 | 7 | 10 | 10 |
| Trisodium citrate | 8 | 5 | 3 | 3 |
| Acrylic Acid/Maleic Acid copolymer | 7 | 5 | 7 | 8 |
| Diethylenetriamine penta(methylene phosphonic acid) | 0.4 | 0 | 0 | 0 |
| EDDS | 0 | 0.3 | 0.5 | 0.5 |
| Carboxymethylcellulose | 0 | 0.4 | 0 | 0 |
| Protease | 1.1 | 2.4 | 0.3 | 1.1 |
| Lipolase | 0 | 0.2 | 0 | 0 |
| Carezyme | 0 | 0.2 | 0 | 0 |
| Anionic soil release polymer | 0.5 | 0.4 | 0.5 | 0.5 |
| Dye transfer inhibiting polymer | 0.3 | 0.02 | 0 | 0.3 |
| Carbonate | 21 | 10 | 13 | 14 |
| Sulfate, Water, Perfume, Colorants | to 100 | to 100 | to 100 | to 100 |

*Quaternary substituted bleach activator according to any of Examples I to V.

EXAMPLE VII

A simple, effective fabric bleach designed to be dissolved in water prior to use is as follows:

| Ingredient | % (wt.) |
|---|---|
| Quaternary Substituted Bleach Activator* | 7.0 |
| Sodium Perborate (monohydrate) | 50.0 |
| Chelant (EDDS) | 10.0 |
| Sodium Silicate | 5.0 |
| Sodium Sulfate | Balance |

*QSBA according to any of Examples I-V.

In an alternate embodiment, the composition is modified by replacing the sodium perborate with sodium percarbonate.

EXAMPLE VIII

A simple, yet effective, fabric bleach designed to be dissolved in water prior to use is as follows:

| Ingredient | % (wt.) |
|---|---|
| Quaternary Substituted Bleach Activator* | 7.0 |
| Sodium Perborate (monohydrate) | 50.0 |
| $C_{12}$ Alkyl Sulfate, Na | 4.5 |
| Citric acid | 6.0 |
| $C_{12}$ Pyrrolidone | 0.6 |
| Chelant (DTPA) | 0.5 |
| Perfume | 0.4 |
| Filler and water | Balance to 100% |

*QSBA according to any of Examples I-V.

The composition is prepared by admixing the indicated ingredients. In an alternate embodiment, the composition is modified by replacing the sodium perborate with sodium percarbonate.

EXAMPLE IX

A simple, yet effective, fabric bleach designed to be dissolved in water prior to use is as follows:

| Ingredient | % (wt.) |
|---|---|
| Quaternary Substituted Bleach Activator* | 7.0 |
| Sodium Perborate (monohydrate) | 30.0 |
| Zeolite A | 20.0 |
| Chelant | 3.0 |
| $C_{12}$ Alkyl Sulfate, Na | 4.5 |
| Citric Acid | 6.0 |
| $C_{12}$ Pyrrolidone | 0.7 |
| Perfume | 0.4 |
| Filler and water | Balance to 100% |

*QSBA according to any of Examples I-V.

The composition is prepared by admixing the indicated ingredients. In an alternate embodiment, the composition is modified by replacing the sodium perborate with sodium percarbonate. In an alternate embodiment, the composition is modified by replacing the Zeolite A with Zeolite P.

EXAMPLE X

An abrasive thickened liquid composition especially useful for cleaning bathtubs and shower tiles is formed upon addition of the following composition to water.

| Ingredient | % (wt.) |
|---|---|
| Quaternary Substituted Bleach Activator* | 7.0 |
| Sodium Perborate (monohydrate) | 50.0 |
| $C_{12}$AS, Na | 5.0 |
| $C_{12-14}$ $AE_3S$, Na | 1.5 |
| $C_8$ Pyrrolidone | 0.8 |
| Oxydisuccinic Acid | 0.5 |
| Sodium citrate | 5.5 |
| Calcium carbonate abrasive(15–25 micrometer) | 15.0 |
| Filler and water | Balance to 100% |
| Product pH upon dilution | Adjust to 10 |

*QSBA according to any of Examples I-V.

EXAMPLE XI

A composition, which provides benefits with respect to the removal of soil from shower walls and bathtubs, is formed upon addition of the following composition in water.

| Ingredient | % (wt.) |
| --- | --- |
| Quaternary Substituted Bleach Activator* | 7.0 |
| Sodium Perborate (monohydrate) | 50.0 |
| $C_{12}AS$, Na | 5.0 |
| $C_8E_4$ Nonionic | 1.0 |
| Sodium citrate | 6.0 |
| $C_{12}$ Pyrrolidone | 0.75 |
| Perfume | 0.6 |
| Filler and water | Balance to 100% |

*QSBA according to any of Examples I–V.

EXAMPLE XII

A granular automatic dishwashing detergent composition comprises the following.

| Example XII INGREDIENT | A wt % | B wt % | C wt % | D wt % |
| --- | --- | --- | --- | --- |
| QSBA (See Note 1) | 3 | 4.5 | 2.5 | 4.5 |
| Sodium Perborate Monohydrate (See Note 2) | 1.5 | 0 | 1.5 | 0 |
| Sodium Percarbonate (See Note 2) | 0 | 1.2 | 0 | 1.2 |
| Amylase (TERMAMYL ® from NOVO) | 2 | 2 | 2 | 2 |
| Dibenzoyl Peroxide | 0 | 0 | 0.8 | 0 |
| Transition Metal Bleach Catalyst (See Note 3) | 0.1 | 0.1 | 0.1 | 0 |
| Nonquaternary Bleach Activator (TAED or NOBS) | 1 | 0 | 3 | 0 |
| Protease (SAVINASE ® 12 T, NOVO, 3.6% active protein) | 2.5 | 2.5 | 2.5 | 2.5 |
| Trisodium Citrate Dihydrate (anhydrous basis) | 15 | 15 | 15 | 15 |
| Sodium Carbonate, anhydrous | 20 | 20 | 20 | 20 |
| BRITESIL H20 ®, PQ Corp. (as $SiO_2$) | 10 | 8 | 7 | 5 |
| Diethylenetriaminepenta(methylenephosphonic acid), Na | 0 | 0 | 0 | 0.2 |
| Hydroxyethyldiphosphonate (HEDP), Sodium Salt | 0 | 0.5 | 0 | 0.5 |
| Ethylenediaminedisuccinate, Trisodium Salt | 0.1 | 0.3 | 0 | 0 |
| Dispersant Polymer (Accusol 480N) | 8 | 5 | 8 | 10 |
| Nonionic Surfactant (LF404, BASF) | 1.5 | 1.5 | 1.5 | 1.5 |
| Paraffin (Winog 70 ®) | 1 | 1 | 1 | 0 |
| Benzotriazole | 0.1 | 0.1 | 0.1 | 0 |
| Sodium Sulfate, water, minors BALANCE TO: | 100% | 100% | 100% | 100% |

Note 1:QSBA: QSBA is the final product of Example I. This QSBA may be substituted by use of a QSBA according to any of Examples II–V.
Note 2:These hydrogen peroxide sources are expressed on a weight % available oxygen basis. To convert to a basis of percentage of the total composition, divide by about 0.15.
Note 3:Transition Metal Bleach Catalyst: MnEDDS according to U.S. application Ser. No. 08/210,186, filed March 17, 1994.

EXAMPLE XIII

This Example illustrates several liquid bleach compositions in accordance with the invention, all of which are made by the general process described hereinafter. The desired amount of a chelating agent is added to a beaker of water, after which the resulting solution is stirred until the chelating agent is completely dissolved. A phase stabilizer is added to the solution while it is being continuously stirred. Thereafter, the bleach activator and optionally an additional chelating agent is added to the solution. The pH of the solution is adjusted to about 4.0 with an alkaline adjusting agent such as sodium hydroxide.

The following translucent, stable aqueous liquid bleach compositions (Samples A–F) are made as described above, all amounts being expressed as percentages by weight.

TABLE I

| Example XII Ingredients | A wt % | B wt % | C wt % | D wt % |
| --- | --- | --- | --- | --- |
| Water | 76 | 81 | 84 | 70 |
| NEODOL 91-10[1] | 10 | 10 | 10 | 10 |
| NEODOL 23-2[1] | — | — | — | 5 |
| DEQUEST 2010[2] | 0.5 | 0.1 | 0.1 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Hydrogen Peroxide | 7 | 3 | 2 | 7 |

[1]Alkyl ethoxylate available from The Shell Oil Company.
[2]Hydroxy-ethylidene diphosphonic acid commercially available from Monsanto Co.
[3]QSBA according to any of Examples I–V.

TABLE II

| Example XIII Ingredients | E wt % | F wt % | G wt % |
| --- | --- | --- | --- |
| Water | 73 | 75 | 71 |
| NEODOL 91-10[1] | 10 | 10 | 10 |
| NEODOL 23-2[1] | 5 | 5 | 5 |
| DEQUEST 2010[2] | 0.5 | 0.5 | 1.0 |
| QSBA[3] | 4 | 4 | 8 |
| Citric Acid | 0.5 | 0.5 | 0.5 |
| NaOH | to pH 4 | to pH 4 | to pH 4 |
| Hydrogen Peroxide | 7 | 5 | 5 |

[1]Alkyl ethoxylate available from The Shell Oil Company.
[2]Hydroxy-ethylidene diphosphonic acid commercially available from Monsanto Co.
[3]Bleach activator according to any of Examples I–V.

EXAMPLE XIV

A laundry bar suitable for hand-washing soiled fabrics is prepared comprising the following ingredients.

| Component | Weight % |
| --- | --- |
| $C_{12}$ linear alkyl benzene sulfonate | 30 |
| Phosphate (as sodium tripolyphosphate) | 7 |
| Sodium carbonate | 15 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| QSBA** | 6.5 |
| Sodium percarbonate | 15 |
| Brightener, perfume | 0.2 |
| Protease | 0.3 |
| $CaSO_4$ | 1 |
| $MgSO_4$ | 1 |
| Water and Filler* | Balance to 100% |

*Can be selected from convenient materials such as $CaCO_3$, talc, clay, silicates, and the like.
**Bleach Activator according to any of Examples I–V.

Detergent laundry bar is extruded in conventional soap or detergent bar making equipment as commonly used in the art.

EXAMPLE XV

A laundry bar suitable for hand-washing soiled fabrics is prepared comprising the following ingredients.

| Component | Weight % |
|---|---|
| Linear alkyl benzene sulfonate | 30 |
| Phosphate (as sodium tripolyphosphate) | 7 |
| Sodium carbonate | 20 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| QSBA** | 5 |
| Sodium perborate tetrahydrate | 10 |
| Brightener, perfume | 0.2 |
| Protease | 0.3 |
| CaSO$_4$ | 1 |
| MgSO$_4$ | 1 |
| Water | 4 |
| Filler* | Balance to 100% |

*Can be selected from convenient materials such as CaCO$_3$, talc, clay, silicates, and the like.
**Bleach Activator according to any of Examples I–V.

A detergent laundry bar is extruded in conventional soap or detergent bar making equipment as commonly used in the art with the bleaching activator dry-mixed with the perborate bleaching compound and not affixed to the surface of the perborate.

EXAMPLE XVI

Liquid bleaching compositions for cleaning typical householud surfaces are as follows. The hydrogen peroxide is separated as an aqueous solution from the other components by a suitable means such as a dual chamber container.

| Component | A wt % | B wt % |
|---|---|---|
| C$_{8-10}$E$_6$ nonionic surfactant | 20 | 15 |
| C$_{12-15}$E$_3$ nonionic surfactant | 4 | 4 |
| C$_8$ alkyl sulfate anionic surfactant | 0 | 7 |
| Na$_2$CO$_3$/NaHCO$_3$ | 1 | 2 |
| C$_{12-18}$ Fatty Acid | 0.6 | 0.4 |
| Hydrogen peroxide | 7 | 7 |
| QSBA** | 7 | 7 |
| DEQUEST 2010* | 0.05 | 0.05 |
| H$_2$O | Balance to 100 | Balance to 100 |

*Hydroxy-ethylidene diphosphonic acid commercially available from Monsanto Co.
**Bleach Activator according to any of Examples I–V.

What is claimed is:

1. A bleaching composition comprising:
   (a) from about 0.1% to about 50% by weight of the composition of a source of hydrogen peroxide; and
   (b) from about 0.1% to about 50% by weight of the composition of a quaternary substituted bleach activator comprising:
   (I) quaternary moieties QC(X)L; and
   (II) a charge balancing number of compatible counterions; provided that:
   1) L is a leaving group and comprises at least one tri-coordinate nitrogen atom covalently connecting L to the moiety —C(X)— wherein LH, the conjugate acid of L, is non-charged or anionically charged and wherein the conjugate acid aqueous pK$_a$ of said L with respect to said tri-coordinate nitrogen atom is about 13 or greater; L is selected from the group consisting of cyclic amidines having a ring size of from about 5 to about 12 atoms, anilino derivatives, and mixtures thereof;

2) Q comprises a tetravalent nitrogen atom, N$^+$, wherein the tetravalent nitrogen atom is covalently connected to the moiety —C(X)L by a single, double, triple aliphatic, aromatic, or alkaryl linkage, and further wherein the atom Q to which the moiety —C(X)— is bonded is a carbon atom; when the linkage is aliphatic, the linkage comprises at least two carbon atoms between the tetravalent nitrogen atom and the moiety —C(X)—; and X is selected from the group consisting of =O, =N— and =S; and further provided that the quaternary substituted bleach activator has a ratio of:

(i) k$_P$/k$_H$ ≧ 1 wherein k$_P$ is the rate constant for perhydrolysis of the quaternary substituted bleach activator and k$_H$ is the rate constant for hydrolysis of the quaternary substituted bleach activator; and a ratio of:

(ii) k$_P$/k$_D$ > 5 wherein k$_P$ is as defined in (i) and wherein k$_D$ is the rate constant for formation of a diacylperoxide from the quaternary substituted bleach activator; and further provided that k$_H$ ≧ 10 M$^{-1}$ s$^{-1}$.

2. A bleaching composition according to claim 1 wherein L is a cyclic amidine with a ring size of from about 5 to about 7 atoms.

3. A method for removing stains from fabrics, dishware, or hard surfaces, comprising contacting said stains in an aqueous solution, dispersion or slurry comprising a bleaching composition according to claim 1.

4. A bleaching composition according to claim 1 wherein L is non-charged; Q contains no charged moieties other than said tetravalent nitrogen; said compatible counterions are anions or polyanions; X is O; said pK$_a$ of L is less than or equal to about 33 as measured in DMSO; k$_P$/k$_H$ ≧ 2; and k$_P$/k$_D$ ≧ 50.

5. A bleaching composition according to claim 4 in which said quaternary substituted bleach activator has a perhydrolysis efficiency of at least 10% and has k$_P$/k$_H$ ≧ 4.

6. A bleaching composition according to claim 1 further comprising conventional bleach activators.

7. A bleaching composition according to claim 6 wherein said conventional bleach activator is selected from the group consisting of alkanoyloxybenzenesulfonates, tetraacetylethylenediamine, and mixtures thereof.

8. A bleaching composition according to claim 6 further comprising a transition-metal containing bleach catalyst.

9. A bleaching composition according to claim 1 wherein said quaternary substituted bleach activator comprises at least one electron-withdrawing substituent in Q, such that the pK$_a$ of QC(X)OOH is less than the pK$_a$ of the nonsubstituted form.

10. A bleaching composition according to claim 9 wherein said electron-withdrawing substituent is neutrally-charged.

11. A bleaching composition according to claim 9 wherein said electron-withdrawing substituent is nitro.

12. A bleaching composition according to claim 1 wherein L is

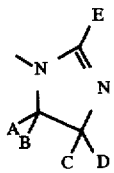

wherein A, B, C, D and E are selected from the group consisting of H, substituted or unsubstituted alkyl, ethoxylated alkyl, linear alkyl, aryl, alkaryl, substituted alkaryl, substituted aryl and mixtures thereof.

13. A bleaching composition according to claim 12 wherein E is methyl and wherein A, B, C and D are hydrogen.

14. A bleaching composition according to claim 12 wherein Q is contained within a ring.

15. A bleaching composition according to claim 12 further comprising a bleach-stable thickener.

16. A bleaching composition according to claim 12 further comprising at least one ethoxylated nonionic surfactant.

17. A bleaching composition according to claim 12 further comprising at least one anionic surfactant, provided that said quaternary bleach activator does not react with said anionic surfactant to form a visible percipitate at ambient temperature.

18. A bleaching composition according to claim 12 wherein said quaternary substituted bleach activator is surface-active, having a critical micelle concentration of less than or equal to about $10^{-2}$ molar and comprising one long-chain moiety having a chain of from about 8 to about 12 atoms and wherein the counter-ion is non surface-active.

19. A bleaching composition according to claim 12 wherein Q is selected from $R^1R^2R^3N^+T$ wherein $R^1$, $R^2$ and $R^3$ can vary independently and each of said R moieties is selected from the group consisting of H, methyl, ethyl, $C_n$ linear or branched, substituted or unsubstituted alkyl wherein n is from 3 to about 16, aryl, substituted aryl, alkaryl, substituted alkaryl, and ethoxylated alkyl; and T is selected form the group consisting of —$(CH_2)_i$— wherein i is from about 3 to about 12, —$(CH_2)_i(C_6H_4)(CH_2)_j$— wherein i and j are independently from 0 to about 12 provided that at least one of i and j is nonzero and the polyalkylene substituents attached to $C_6H_4$ are o-, m- or p- to each other, -(Aryl)-, -(Alkyl)G(Aryl)-, -(Alkyl)G(Alkyl)-, -(Aryl)G(Alkyl)-, and -(Aryl)G(Aryl)-; wherein G is selected from the group consisting of O, —C(O)N($R^4$)—, —S(O)$_2$N($R^4$)—, —N($R^4$)(C(O)—, —N($R^4$)S(O)$_2$—, —S(O)$_2$— and —N($R^4$)C(O)N($R^5$)—; wherein $R^4$ and $R^5$ are H or alkyl.

20. A bleaching composition according to claim 19 wherein said quaternary substituted bleach activator comprises:

$R^1R^2R^3N^{3+}TC(O)L$: 

wherein $R^1$, $R^2$ and $R^3$ can vary independently and are selected form: H, methyl, ethyl, phenyl, benzyl, 1-naphthylmethylene and 2-naphthylmethylene; and T is selected from: m-$C_6H_4$, p-$C_6H_4$, —$(CH_2)_i$(m-$C_6H_4$)—, and —$(CH_2)_i$(p-$C_6H_4$)—; wherein i is from 1 to about 6.

21. A bleaching composition according to claim 12 further comprising a low-foaming automatic dishwashing surfactant.

22. A bleaching composition according to claim 21 having granular automatic dishwashing detergent form comprising:
 a) from about 0.1% to about 10% of said quaternary substituted bleach activator;
 b) from about 0.5% to about 25% of said source of hydrogen peroxide in the form of a perborate or percarbonate salt; and
 c) from about 0.1% to about 7% of said surfactant.

23. A bleaching composition according to claim 12 further comprising a laundry detergent surfactant.

24. A bleaching composition according to claim 23 wherein said laundry detergent surfactant is selected from the group consisting of sugar-derived surfactants, amine oxides, sarcosinates and mixtures thereof.

25. A bleaching composition according to claim 23 in granular laundry detergent form comprising:

a) from about 0.1% to about 10% of said quaternary substituted bleach activator;
 b) from about 0.5% to about 25% of said source of hydrogen peroxide in the form of a perborate or percarbonate salt; and
 c) from about 0.5% to about 25% of said surfactant.

26. A bleaching composition according to claim 23 further comprising a detergent builder.

27. A bleaching composition according to claim 26 wherein said detergent builder is selected from the group consisting of: citrate, layered silicate, zeolite A, zeolite P and mixtures thereof.

28. A bleaching composition comprising:
 (a) from about 0.1% to about 50% by weight of the composition of a source of hydrogen peroxide; and
 (b) from about 0.1% to about 50% by weight of the composition of a quaternary substituted bleach activator comprising:
  (I) quaternary moieties QC(X)L; and
  (II) a charge balancing number of compatible counterions; provided that:
   1) L is a leaving group and comprises at least one tri-coordinate nitrogen atom covalently connecting L to the moiety —C(X)— wherein LH, the conjugate acid of L, is non-charged or anionically charged and wherein the conjugate acid aqueous p$K_a$ of said L with respect to said tri-coordinate nitrogen atom is about 13 or greater; L is a lactam with a ring size of from about 6 to about 12;
   2) Q comprises a tetravalent nitrogen atom, $N^+$, wherein the tetravalent nitrogen atom is covalently connected to the moiety —C(X)L by a single, double, triple aliphatic, aromatic, or alkaryl linkage, and further wherein the atom Q to which the moiety —C(X)— is bonded is a carbon atom; when the linkage is aliphatic, the linkage comprises at least two carbon atoms between the tetravalent nitrogen atom and the moiety —C(X)—; and X is selected form the group consisting of =N— and =S; and further provided that the quaternary substituted bleach activator has a ratio of:
   (i) $k_P/k_H \geq 1$ wherein $k_P$ is the rate constant for perhydrolysis of the quaternary substituted bleach activator and $k_H$ is the rate constant for hydrolysis of the quaternary substituted bleach activator; and a ratio of:
   (ii) $k_P/k_D \geq 5$ wherein $k_P$ is as defined in (i) and wherein $k_D$ is the rate constant for formation of a diacylperoxide from the quaternary substituted bleach activator; and further provide that $k_H \leq 10M^{-1} s^{-1}$.

29. A bleaching composition according to claim 28 further comprising a member selected from the group consisting of a detersive surfactant, a low-foaming automatic dishwashing surfactant, and a bleach-stable thickener.

30. A bleaching composition according to claim 28 in granular laundry detergent form comprising:
 a) from about 0.1% to about 10% of said bleach activator;
 b) from about 0.5% to about 25% of said source of hydrogen peroxide in the form of a perborate or percarbonate salt; and
 c) from about 0.5% to about 25% of surfactant.

* * * * *

UNITED STATES PATENT AND TRADEMARK OFFICE
CERTIFICATE OF CORRECTION

PATENT NO. : 5,686,015
DATED : November 11, 1997
INVENTOR(S) : Alan David Willey et al.

It is certified that error appears in the above-identified patent and that said Letters Patent is hereby corrected as shown below:

Column 41, line 43 should read --$R^1R^2R^3N^+TC(O)L$;--.
Column 41, line 45 "form" should read --from--.

Column 42, line 51 "provide" should read --provided--.

Signed and Sealed this

Eleventh Day of May, 1999

Attest:

Q. TODD DICKINSON

Attesting Officer

Acting Commissioner of Patents and Trademarks